(12) United States Patent
Nishi et al.

(10) Patent No.: US 9,206,168 B2
(45) Date of Patent: Dec. 8, 2015

(54) (2-HETEROARYLAMINO) SUCCINIC ACID DERIVATIVES

(71) Applicant: Daiichi Sankyo Company, Limited, Tokyo (JP)

(72) Inventors: Tatsuya Nishi, Tokyo (JP); Naoki Tanaka, Tokyo (JP); Ryoko Kitazawa, Tokyo (JP); Riki Goto, Tokyo (JP); Takashi Ishiyama, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/495,337

(22) Filed: Sep. 24, 2014

(65) Prior Publication Data

US 2015/0011574 A1    Jan. 8, 2015

Related U.S. Application Data

(63) Continuation of application No. PCT/JP2013/059657, filed on Mar. 29, 2013.

(30) Foreign Application Priority Data

Mar. 30, 2012   (JP) ................. 2012-079859

(51) Int. Cl.

| | | |
|---|---|---|
| *A61K 47/10* | (2006.01) | |
| *C07D 405/14* | (2006.01) | |
| *C07D 213/75* | (2006.01) | |
| *C07D 213/82* | (2006.01) | |
| *C07D 401/12* | (2006.01) | |
| *C07D 239/47* | (2006.01) | |
| *A61K 9/00* | (2006.01) | |
| *A61K 9/20* | (2006.01) | |
| *A61K 9/48* | (2006.01) | |
| *C07C 53/18* | (2006.01) | |

(52) U.S. Cl.
CPC ............ *C07D 405/14* (2013.01); *A61K 9/0019* (2013.01); *A61K 9/2013* (2013.01); *A61K 9/2018* (2013.01); *A61K 9/2054* (2013.01); *A61K 9/4858* (2013.01); *A61K 9/4866* (2013.01); *A61K 47/10* (2013.01); *C07C 53/18* (2013.01); *C07D 213/75* (2013.01); *C07D 213/82* (2013.01); *C07D 239/47* (2013.01); *C07D 401/12* (2013.01)

(58) Field of Classification Search
CPC .. C07D 405/14; C07D 213/75; C07D 213/82; C07D 401/12; C07D 239/47; C07D 53/18; A61K 9/4866; A61K 47/10; A61K 9/2013; A61K 9/2018; A61K 9/2054; A61K 9/4858; A61K 9/0019

See application file for complete search history.

(56) References Cited

U.S. PATENT DOCUMENTS

| | | | |
|---|---|---|---|
| 6,239,109 B1 * | 5/2001 | Rodgers et al. | 514/7.7 |
| 7,799,827 B2 * | 9/2010 | Boivin et al. | 514/450 |
| 8,329,742 B2 * | 12/2012 | Boivin et al. | 514/450 |
| 8,785,462 B2 * | 7/2014 | Kuribayashi et al. | 514/269 |
| 2006/0247448 A1 * | 11/2006 | Boivin et al. | 549/269 |
| 2011/0112103 A1 | 5/2011 | Kuribayashi et al. | |
| 2011/0144101 A1 * | 6/2011 | Boivin et al. | 514/233.5 |
| 2012/0220609 A1 | 8/2012 | Kuribayashi et al. | |
| 2013/0196987 A1 * | 8/2013 | Boivin et al. | 514/233.5 |

FOREIGN PATENT DOCUMENTS

| | | |
|---|---|---|
| JP | 2011-088840 | 5/2011 |
| JP | 2011-105708 | 6/2011 |
| WO | WO 2009/117269 A1 | 9/2009 |
| WO | WO 2009/131127 A1 | 10/2009 |
| WO | WO 2009/131129 A1 | 10/2009 |
| WO | WO 2011/002623 A1 | 1/2011 |
| WO | WO 2011/002624 A1 | 1/2011 |
| WO | WO 2011/049126 A1 | 4/2011 |
| WO | WO 2011/049127 A1 | 4/2011 |
| WO | WO 2011/132633 A1 | 10/2011 |

OTHER PUBLICATIONS

CAS Registry No. 1348918-49-9 (Dec. 5, 2005).*
International Search Report issued in related International Patent Application No. PCT/JP2013/059657, completed Jun. 4, 2013.

* cited by examiner

Primary Examiner — Alexander R Pagano
(74) *Attorney, Agent, or Firm* — Foley & Lardner LLP

(57) ABSTRACT

The present invention provides a compound which enhances the production of erythropoietin. The present invention provides a compound represented by the formula (1) wherein $R^1$: an aromatic hydrocarbon ring group or an aromatic heterocyclic group; $R^2$: a hydrogen atom, an alkyl group, or a heterocycloalkyl group; $R^3$: a hydrogen atom or an alkyl group; A: a hydrogen atom or a hydroxy group; L: —NHCO— or —OCH$_2$—; and X: a nitrogen atom or =CH—.

16 Claims, No Drawings

(2-HETEROARYLAMINO) SUCCINIC ACID DERIVATIVES

This application is a continuation of International Patent Application No. PCT/JP2013/059657, filed Mar. 29, 2013, which claims priority from Japanese Patent Application No. 2012-079859, filed Mar. 30, 2012. The contents of these applications are incorporated herein by reference in their entirety.

TECHNICAL FIELD

The present invention relates to low molecular weight compounds having an erythropoietin production-enhancing activity.

BACKGROUND ART

Erythropoietin (hereinafter abbreviated as EPO) is a glycoprotein hormone that is essential for erythrocyte hematopoiesis. It is normally secreted from the kidneys and promotes production of erythrocytes by acting on erythrocyte stem cells present in bone marrow. In diseases presenting with a decrease in intrinsic EPO production (such as chronic renal failure), since erythrocyte production decreases and symptoms of anemia are exhibited, treatment is provided in the form of replacement therapy using gene-recombinant human EPO. However, this gene-recombinant human EPO has been indicated as having shortcomings such as being a biological preparation and associated with expensive health care costs, having poor convenience due to being an injection and having antigenicity.

On the other hand, compounds such as 4-hydroxypyrimidine-5-carboxamide derivatives (see Patent Documents 1 to 3) and 5-hydroxypyrimidine-4-carboxamide derivatives (see Patent Documents 4 to 8) are known to be low molecular weight EPO inducers.

PRIOR ART DOCUMENTS

Patent Documents

Patent Document 1: International Publication No. WO 2009/117269
Patent Document 2: International Publication No. WO 2011/002623
Patent Document 3: International Publication No. WO 2011/002624
Patent Document 4: International Publication No. WO 2009/131127
Patent Document 5: International Publication No. WO 2009/131129
Patent Document 6: International Publication No. WO 2011/049126
Patent Document 7: International Publication No. WO 2011/049127
Patent Document 8: International Publication No. WO 2011/132633

SUMMARY OF INVENTION

Technical Problem of the Invention

The inventors of the present invention conducted studies for the purpose of providing novel low molecular weight compounds that have a superior EPO production-enhancing activity and that are useful for the treatment of diseases caused by decreased EPO, and for the purpose of providing a medicament containing such compounds.

Means for Solution to the Problem

In order to solve the aforementioned problems, the inventors of the present invention found that novel compounds having a (2-heteroarylamino)succinic acid structure have a superior EPO production-enhancing activity and that they are effective for treating diseases caused by decreased EPO, thereby leading to completion of the present invention.

According to the present invention, novel (2-heteroarylamino)succinic acid compounds represented by the following general formula (1) or pharmacologically acceptable salts thereof (hereinafter collectively referred to as compounds of the present invention), are provided.

Specifically, the present invention provides:
(1) a compound represented by the following general formula (1):

[Formula 1]

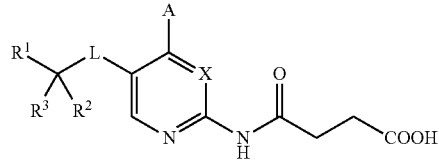

or a pharmacologically acceptable salt thereof, wherein
$R^1$ represents an aromatic hydrocarbon ring group which may have 1 or 2 substituents independently selected from substituent group α, or an aromatic heterocyclic group which may have 1 or 2 substituents independently selected from substituent group α;
substituent group α represents the group consisting of a halogen atom, a $C_1$-$C_4$ alkyl group, a halo $C_1$-$C_4$ alkyl group, a $C_1$-$C_4$ alkoxy group, a $C_3$-$C_6$ cycloalkyl group, and an aromatic hydrocarbon ring group which may be substituted with $R^4$;
$R^2$ represents a hydrogen atom, a $C_1$-$C_4$ alkyl group, or a 4- to 7-membered heterocycloalkyl group;
$R^3$ represents a hydrogen atom or a $C_1$-$C_4$ alkyl group;
$R^4$ represents a cyano group, a halogen atom, or a $C_1$-$C_4$ alkoxy group;
A represents a hydrogen atom or a hydroxy group;
L represents a group represented by the formula —NHCO— or a group represented by the formula —OCH$_2$—; and
X represents a nitrogen atom or a group represented by the formula =CH—,
(2) a compound or a pharmacologically acceptable salt thereof according to (1), wherein $R^1$ is a phenyl group, a naphthyl group, a pyridyl group, a pyrimidinyl group, a pyrazinyl group, or a pyridazinyl group which may have 1 or 2 substituents independently selected from substituent group α,
(3) a compound or a pharmacologically acceptable salt thereof according to (1), wherein $R^1$ is a phenyl group, a naphthyl group, or a pyridyl group which may have 1 or 2 substituents independently selected from substituent group α,
(4) a compound or a pharmacologically acceptable salt thereof according to (1), wherein $R^1$ is a phenyl group or a pyridyl group which may have 1 or 2 substituents independently selected from substituent group α,
(5) a compound or a pharmacologically acceptable salt thereof according to any one of (1) to (4), wherein
the substituent group α is the group consisting of a fluorine atom, a chlorine atom, a methyl group, a trifluoromethyl group, a methoxy group, a cyclopentyl group, and a phenyl group which may be substituted with $R^4$, and
$R^4$ is a cyano group or a methoxy group,
(6) a compound or a pharmacologically acceptable salt thereof according to any one of (1) to (4), wherein
the substituent group α is the group consisting of a fluorine atom, a chlorine atom, a trifluoromethyl group, a methoxy group, and a phenyl group which may be substituted with $R^4$, and
$R^4$ is a methoxy group,
(7) a compound or a pharmacologically acceptable salt thereof according to any one of (1) to (6), wherein $R^2$ is a hydrogen atom, a methyl group, or a tetrahydropyranyl group,
(8) a compound or a pharmacologically acceptable salt thereof according to any one of (1) to (7), wherein $R^3$ is a hydrogen atom or a methyl group,
(9) a compound or a pharmacologically acceptable salt thereof according to any one of (1) to (8), wherein A is a hydroxy group,
(10) a compound or a pharmacologically acceptable salt thereof according to any one of (1) to (9), wherein L is a group represented by the formula —NHCO—,
(11) a compound or a pharmacologically acceptable salt thereof according to any one of (1) to (10), wherein X is a nitrogen atom,
(12) a compound or a pharmacologically acceptable salt thereof according to (1) above, selected from the following:
4-({5-[(2,4-dichlorophenyl)methylcarbamoyl]-4-hydroxypyrimidin-2-yl}amino)-4-oxobutanoic acid,
4-({5-[(2,4-difluorophenyl)methylcarbamoyl]-4-hydroxypyrimidin-2-yl}amino)-4-oxobutanoic acid,
4-({5-[(2-chloro-4-fluorophenyl)methylcarbamoyl]-4-hydroxypyrimidin-2-yl}amino)-4-oxobutanoic acid,
4-{[4-hydroxy-5-(p-tolylmethylcarbamoyl)pyrimidin-2-yl]amino}-4-oxobutanoic acid,
4-({5-[(4-fluoro-3-phenylphenyl)methylcarbamoyl]-4-hydroxypyrimidin-2-yl}amino)-4-oxobutanoic acid,
4-({4-hydroxy-5-[(3-phenylphenyl)methylcarbamoyl]pyrimidin-2-yl}amino)-4-oxobutanoic acid,
4-[(5-{[4-(2-cyanophenyl)phenyl]methylcarbamoyl}-4-hydroxypyrimidin-2-yl)amino]-4-oxobutanoic acid,
4-[(5-{[3-(2-cyanophenyl)phenyl]methylcarbamoyl}-4-hydroxypyrimidin-2-yl)amino]-4-oxobutanoic acid,
4-[(4-hydroxy-5-{[(6-methoxypyridin-3-yl)(tetrahydro-2H-pyran-4-yl)methyl]carbamoyl}pyrimidin-2-yl)amino]-4-oxobutanoic acid,
4-{[4-hydroxy-5-({1-[6-(4-methoxyphenyl)pyridin-3-yl]-1-methylethyl}carbamoyl)pyrimidin-2-yl]amino}-4-oxobutanoic acid,
4-[(4-hydroxy-5-{[3-(trifluoromethyl)phenyl]methylcarbamoyl}pyrimidin-2-yl)amino]-4-oxobutanoic acid,
4-({5-[(3-fluorophenyl)methylcarbamoyl]-4-hydroxypyrimidin-2-yl}amino)-4-oxobutanoic acid,
4-({5-[(3,4-difluorophenyl)methylcarbamoyl]-4-hydroxypyrimidin-2-yl}amino)-4-oxobutanoic acid,
4-{[4-hydroxy-5-(m-tolylmethylcarbamoyl)pyrimidin-2-yl]amino}-4-oxobutanoic acid,
4-{[4-hydroxy-5-(1-naphthylmethylcarbamoyl)pyrimidin-2-yl]amino}-4-oxobutanoic acid,
4-{[4-hydroxy-5-(2-naphthylmethylcarbamoyl)pyrimidin-2-yl]amino}-4-oxobutanoic acid,
4-({5-[(3-cyclopentylphenyl)methylcarbamoyl]-4-hydroxypyrimidin-2-yl}amino)-4-oxobutanoic acid,
4-({4-hydroxy-5-[(3-phenylphenyl)methylcarbamoyl]-2-pyridyl}amino)-4-oxobutanoic acid,
4-oxo-4-({5-[(4-phenylphenyl)methoxymethyl]-2-pyridyl}amino)butanoic acid, and
4-[(5-{[4-(2-cyanophenyl)phenyl]methoxymethyl}-2-pyridyl)amino]-4-oxobutanoic acid,
(13) a pharmaceutical composition containing as an active ingredient a compound or a pharmacologically acceptable salt thereof according to any one of (1) to (12) above,
(14) a pharmaceutical composition according to (13) above, for the prophylaxis and/or treatment of anemia,
(15) a pharmaceutical composition according to (14) above, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure,
(16) a pharmaceutical composition according to (14) above, wherein the anemia is anemia incidental to chronic kidney disease,
(17) a pharmaceutical composition according to (13) above, for producing erythropoietin,
(18) use of a compound or a pharmacologically acceptable salt thereof according to any one of (1) to (12) above, for producing a medicament,
(19) use according to (18) above, wherein the medicament is a medicament for the prophylaxis and/or treatment of anemia,
(20) use according to (19) above, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure,
(21) use according to (19) above, wherein the anemia is anemia incidental to chronic kidney disease,
(22) a method for producing erythropoietin, comprising: administering a pharmacologically effective amount of a compound or a pharmacologically acceptable salt thereof according to any one of (1) to (12) above to a mammal or bird,
(23) a method for the prophylaxis and/or treatment of a disease, comprising: administering a pharmacologically effective amount of a compound or a pharmacologically acceptable salt thereof according to any one of (1) to (12) above to a mammal,
(24) a method according to (23) above, wherein the disease is anemia,
(25) a method according to (23) above, wherein the disease is nephrogenic anemia, anemia of prematurity, anemia incidental to chronic diseases, anemia incidental to cancer chemotherapy, cancerous anemia, inflammation-associated anemia, or anemia incidental to congestive heart failure,
(26) a method according to (23) above, wherein the disease is anemia incidental to chronic kidney disease,
(27) a method according to any one of (23) to (26) above, wherein the mammal is a human,
(28) a compound or a pharmacologically acceptable salt thereof according to any one of (1) to (12) above, for use in a method for the treatment or prophylaxis of a disease,

(29) a compound or a pharmacologically acceptable salt thereof according to (28) above, wherein the disease is anemia,

(30) a compound or a pharmacologically acceptable salt thereof according to (28) above, wherein the disease is nephrogenic anemia, anemia of prematurity, anemia incidental to chronic diseases, anemia incidental to cancer chemotherapy, cancerous anemia, inflammation-associated anemia, or anemia incidental to congestive heart failure, or

(31) a compound or a pharmacologically acceptable salt thereof according to (28) above, wherein the disease is anemia incidental to chronic kidney disease.

The compounds of the present invention represented by the aforementioned general formula (1) have a (2-heteroarylamino)succinic acid skeleton. A substituent at the 5-position of the heteroaryl ring has 1 or 2 cyclic groups, and these cyclic groups have a specific substituent. The compounds of the present invention or pharmacologically acceptable salts thereof have a superior EPO production-enhancing activity.

The following provides an explanation of substituents in the compounds of the present invention.

A "halogen atom" in the definitions of substituent group α and $R^4$ refers to a fluorine atom, a chlorine atom, a bromine atom, or an iodine atom, preferably a fluorine atom or a chlorine atom.

A "$C_1$-$C_4$ alkyl group" in the definitions of substituent group α, $R^2$, and $R^3$ refers to a straight or branched chain alkyl group having 1 to 4 carbon atoms. Examples include a methyl group, an ethyl group, a propyl group, an isopropyl group, a butyl group, an isobutyl group, a sec-butyl group, and a tert-butyl group. The $C_1$-$C_4$ alkyl group is preferably a methyl group.

A "halo $C_1$-$C_4$ alkyl group" in the definition of substituent group α refers to a group in which 1 to 3 hydrogen atoms on the carbon atom(s) of an aforementioned "$C_1$-$C_4$ alkyl group" are replaced with aforementioned "halogen atom(s)". Examples include a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 2,2,2-trifluoroethyl group, a 2,2,2-trichloroethyl group, a 2-fluoroethyl group, a 2-chloroethyl group, a 2-bromoethyl group, a 2-iodoethyl group, a 3-chloropropyl group, a 4-fluorobutyl group, and a 2,2-dibromoethyl group. The halo $C_1$-$C_4$ alkyl group is preferably a trifluoromethyl group.

A "$C_1$-$C_4$ alkoxy group" in the definitions of substituent group α and $R^4$ refers to a group in which an aforementioned "$C_1$-$C_4$ alkyl group" is bonded to an oxygen atom. Examples include a methoxy group, an ethoxy group, a propoxy group, an isopropoxy group, a butoxy group, an isobutoxy group, a sec-butoxy group, and a tert-butoxy group. The $C_1$-$C_4$ alkoxy group is preferably a methoxy group.

A "$C_3$-$C_6$ cycloalkyl group" in the definition of substituent group α refers to a cycloalkyl group having 3 to 6 carbon atoms. Examples include a cyclopropyl group, a cyclobutyl group, a cyclopentyl group, and a cyclohexyl group. The $C_3$-$C_6$ cycloalkyl group is preferably a cyclopentyl group.

A "4- to 7-membered heterocycloalkyl group" in the definition of $R^2$ refers to a monocyclic saturated heterocyclic group composed of a 4- to 7-membered ring containing 1 or 2 atoms selected from the group consisting of a nitrogen atom, an oxygen atom, and a sulfur atom. Examples include an azetidinyl group, a pyrrolidinyl group, a piperidyl group, an azepanyl group, an oxetanyl group, a tetrahydrofuranyl group, a tetrahydropyranyl group, an oxepanyl group, a tetrahydrothiophenyl group, a tetrahydrothiopyranyl group, an oxazolidinyl group, a thiazolidinyl group, a piperazinyl group, a morpholinyl group, a dioxolanyl group, a dioxanyl group, and a dioxepanyl group. The 4- to 7-membered heterocycloalkyl group is preferably a tetrahydropyranyl group.

An "aromatic hydrocarbon ring group" in the definitions of $R^1$ and substituent group α refers to a monocyclic, bicyclic, or tricyclic aromatic hydrocarbon ring group having 6 to 14 carbon atoms. Examples include a phenyl group, an indenyl group, a naphthyl group, an azulenyl group, a heptalenyl group, a biphenyl group, an indacenyl group, an acenaphthyl group, a fluorenyl group, a phenalenyl group, a phenanthrenyl group, an anthracenyl group, a cyclopentacyclooctenyl group, and a benzocyclooctenyl group. The aromatic hydrocarbon ring group in $R^1$ is preferably a phenyl group or a naphthyl group, more preferably a phenyl group. The aromatic hydrocarbon ring group in substituent group α is preferably a phenyl group.

An "aromatic heterocyclic group" in the definition of $R^1$ refers to a 5- to 10-membered monocyclic or bicyclic aromatic heterocyclic group containing 1 or 2 atoms selected from the group consisting of a nitrogen atom, an oxygen atom, and a sulfur atom. Examples include: monocyclic heterocyclic groups such as a pyrrolyl group, a pyridyl group, a thienyl group, a furyl group, a pyrimidinyl group, a pyranyl group, a pyrazinyl group, a pyridazinyl group, a pyrazolyl group, an imidazolyl group, a thiazolyl group, an isothiazolyl group, an oxazolyl group, and an isooxazolyl group; and bicyclic heterocyclic groups such as a quinolyl group, an isoquinolyl group, a quinazolinyl group, a chromanyl group, an isochromanyl group, a benzofuranyl group, a dihydrobenzofuranyl group, a benzothiophenyl group, a dihydrobenzothiophenyl group, an indolyl group, an isoindolyl group, a quinoxalinyl group, a benzothiazolyl group, a tetrahydroquinolyl group, a tetrahydroisoquinolyl group, a benzoxazolyl group, a benzoxanyl group, an indolizinyl group, a thienopyridyl group, a dihydrothienopyridyl group, a furopyridyl group, a dihydrofuropyridyl group, a benzimidazolyl group, a benzothienyl group, an isobenzofuranyl group, and an indolinyl group. The aromatic heterocyclic group is preferably a pyridyl group, a pyrimidinyl group, a pyrazinyl group, or a pyridazinyl group, more preferably a pyridyl group.

In the compounds of the present invention, $R^1$ represents an aromatic hydrocarbon ring group which may have 1 or 2 substituents independently selected from substituent group α, or an aromatic heterocyclic group which may have 1 or 2 substituents independently selected from substituent group α and is preferably a phenyl group, a naphthyl group, a pyridyl group, a pyrimidinyl group, a pyrazinyl group, or a pyridazinyl group which may have 1 or 2 substituents independently selected from substituent group α, more preferably a phenyl group, a naphthyl group, or a pyridyl group which may have 1 or 2 substituents independently selected from substituent group α, even more preferably a phenyl group or a pyridyl group which may have 1 or 2 substituents independently selected from substituent group α.

In the compounds of the present invention, the substituent group α represents the group consisting of a halogen atom, a $C_1$-$C_4$ alkyl group, a halo $C_1$-$C_4$ alkyl group, a $C_1$-$C_4$ alkoxy group, a $C_3$-$C_6$ cycloalkyl group, and an aromatic hydrocarbon ring group which may be substituted with $R^4$ and is preferably the group consisting of a fluorine atom, a chlorine atom, a methyl group, a trifluoromethyl group, a methoxy group, a cyclopentyl group, and a phenyl group which may be substituted with $R^4$, more preferably the group consisting of a fluorine atom, a chlorine atom, a trifluoromethyl group, a methoxy group, and a phenyl group which may be substituted with $R^4$.

In the compounds of the present invention, $R^4$ represents a cyano group, a halogen atom, or a $C_1$-$C_4$ alkoxy group and is preferably a cyano group or a methoxy group, more preferably a methoxy group.

In the compounds of the present invention, the phenyl group which may be substituted with $R^4$ is preferably a phenyl group or a 4-methoxyphenyl group.

In the compounds of the present invention, $R^2$ represents a hydrogen atom, a $C_1$-$C_4$ alkyl group, or a 4- to 7-membered heterocycloalkyl group and is preferably a hydrogen atom, a methyl group, or a tetrahydropyranyl group.

In the compounds of the present invention, $R^3$ represents a hydrogen atom or a $C_1$-$C_4$ alkyl group and is preferably a hydrogen atom or a methyl group.

In the compounds of the present invention, A represents a hydrogen atom or a hydroxy group and is preferably a hydroxy group.

In the compounds of the present invention, L represents a group represented by the formula —NHCO— or a group represented by the formula —OCH$_2$— and is preferably a group represented by the formula —NHCO—. In this context, a bond shown on the left side in each group refers to being bonded to the carbon atom substituted with $R^1$, $R^2$, and $R^3$.

In the compounds of the present invention, X represents a nitrogen atom or a group represented by the formula =CH— and is preferably a nitrogen atom.

The compound of the present invention is preferably one selected from the following compounds or pharmacologically acceptable salts thereof:

4-({5-[(2,4-dichlorophenyl)methylcarbamoyl]-4-hydroxypyrimidin-2-yl}amino)-4-oxobutanoic acid,
4-({5-[(2,4-difluorophenyl)methylcarbamoyl]-4-hydroxypyrimidin-2-yl}amino)-4-oxobutanoic acid,
4-({5-[(2-chloro-4-fluorophenyl)methylcarbamoyl]-4-hydroxypyrimidin-2-yl}amino)-4-oxobutanoic acid,
4-{[4-hydroxy-5-(p-tolylmethylcarbamoyl)pyrimidin-2-yl]amino}-4-oxobutanoic acid,
4-({5-[(4-fluoro-3-phenylphenyl)methylcarbamoyl]-4-hydroxypyrimidin-2-yl}amino)-4-oxobutanoic acid,
4-({4-hydroxy-5-[(3-phenylphenyl)methylcarbamoyl]pyrimidin-2-yl}amino)-4-oxobutanoic acid,
4-[(5-{[4-(2-cyanophenyl)phenyl]methylcarbamoyl}-4-hydroxypyrimidin-2-yl)amino]-4-oxobutanoic acid,
4-[(5-{[3-(2-cyanophenyl)phenyl]methylcarbamoyl}-4-hydroxypyrimidin-2-yl)amino]-4-oxobutanoic acid,
4-[(4-hydroxy-5-{[(6-methoxypyridin-3-yl)(tetrahydro-2H-pyran-4-yl)methyl]carbamoyl}pyrimidin-2-yl)amino]-4-oxobutanoic acid,
4-{[4-hydroxy-5-({1-[6-(4-methoxyphenyl)pyridin-3-yl]-1-methylethyl}carbamoyl)pyrimidin-2-yl]amino}-4-oxobutanoic acid,
4-[(4-hydroxy-5-{[3-(trifluoromethyl)phenyl]methylcarbamoyl}pyrimidin-2-yl)amino]-4-oxobutanoic acid,
4-({5-[(3-fluorophenyl)methylcarbamoyl]-4-hydroxypyrimidin-2-yl}amino)-4-oxobutanoic acid,
4-({5-[(3,4-difluorophenyl)methylcarbamoyl]-4-hydroxypyrimidin-2-yl}amino)-4-oxobutanoic acid,
4-{[4-hydroxy-5-(m-tolylmethylcarbamoyl)pyrimidin-2-yl]amino}-4-oxobutanoic acid,
4-{[4-hydroxy-5-(1-naphthylmethylcarbamoyl)pyrimidin-2-yl]amino}-4-oxobutanoic acid,
4-{[4-hydroxy-5-(2-naphthylmethylcarbamoyl)pyrimidin-2-yl]amino}-4-oxobutanoic acid,
4-({5-[(3-cyclopentylphenyl)methylcarbamoyl]-4-hydroxypyrimidin-2-yl}amino)-4-oxobutanoic acid,
4-({4-hydroxy-5-[(3-phenylphenyl)methylcarbamoyl]-2-pyridyl}amino)-4-oxobutanoic acid,
4-oxo-4-({5-[(4-phenylphenyl)methoxymethyl]-2-pyridyl}amino)butanoic acid, and
4-[(5-{[4-(2-cyanophenyl)phenyl]methoxymethyl}-2-pyridyl)amino]-4-oxobutanoic acid.

In the compounds of the present invention, geometrical isomers or tautomers may be present depending on the types of substituents. Further, in the case where the compounds of the present invention have an asymmetric carbon atom, optical isomers may be present. These separated isomers (e.g., enantiomers or diastereomers) and mixtures thereof (e.g., racemates or diastereomeric mixtures) are included in the present invention. Further, labeled compounds, namely compounds in which one or more atoms of compounds of the present invention have been substituted with a corresponding radioactive isotope or non-radioactive isotope in an arbitrary ratio, are also included in the present invention.

In the case where the compound of the present invention has a basic group such as an amino group, a pharmacologically acceptable acid addition salt can be formed, if desired. Examples of such acid addition salts include: hydrohalic acid salts such as hydrofluorides, hydrochlorides, hydrobromides, and hydroiodides; inorganic acid salts such as nitrates, perchlorates, sulfates, and phosphates; lower alkanesulfonates such as methanesulfonates, trifluoromethanesulfonates, and ethanesulfonates; aryl sulfonates such as benzenesulfonates and p-toluenesulfonates; organic acid salts such as acetates, trifluoroacetates, malates, fumarates, succinates, citrates, tartrates, oxalates, and maleates; and amino acid salts such as ornithinates, glutamates, and aspartates, and hydrohalic acid salts and organic acid salts are preferred.

In the case where the compound of the present invention has an acidic group such as a carboxy group, generally a pharmacologically acceptable base addition salt can be formed. Examples of such base addition salts include: alkali metal salts such as sodium salts, potassium salts, and lithium salts; alkaline earth metal salts such as calcium salts and magnesium salts; inorganic salts such as ammonium salts; and organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts, and tris(hydroxymethyl)aminomethane salts.

The compounds of the present invention may also be present as a non-solvate or a solvate. Although there are no particular limitations on the solvate provided it is pharmacologically acceptable, preferred specific examples include hydrates and ethanolates. Further, in the case where a nitrogen atom is present in a compound represented by the general formula (1), it may be in the form of an N-oxide, and these solvates and N-oxide forms are also included within the scope of the present invention.

Although the compounds of the present invention can be present in the form of various isomers including geometrical isomers such as a cis form or trans form, tautomers, or optical isomers such as a d form or l form depending on the types of substituents and combinations thereof, the compounds of the present invention also include all the isomers and mixtures of the isomers in any ratio thereof, unless otherwise specifically limited.

Further, the compounds of the present invention can contain a non-natural ratio of isotopes in one or more atoms constituting such compounds. Examples of the isotopes include deuterium ($^2$H; D), tritium ($^3$H; T), iodine-125 ($^{125}$I), and carbon-14 ($^{14}$C). Further, the compounds of the present invention can be radiolabeled with, for example, radioisotopes such as tritium ($^3$H), iodine-125 ($^{125}$I), or carbon-14 ($^{14}$C). A radiolabeled compound is useful as a therapeutic or prophylactic agent, a research reagent (e.g., an assay reagent), and a diagnostic agent (e.g., an in vivo diagnostic imaging agent). The compounds of the present invention containing all ratios of radioactive or non-radioactive isotopes are included within the scope of the present invention.

The compounds of the present invention can also be produced by applying various known synthesis methods depending on the basic skeleton thereof or types of substituents. In so doing, depending on the types of functional groups, it is possible to protect this functional group with a suitable protecting group at stages from a raw material to an intermediate, or replace it with a group that can be easily converted to this functional group. Examples of such functional groups include an amino group, a hydroxy group, and a carboxy group. Examples of their protecting groups include those described in, for example, Greene and Wuts, "Protective Groups in Organic Synthesis", 3rd ed., 1999, and these protecting groups can be appropriately selected and used depending on the reaction conditions thereof. According to such methods, a desired compound can be obtained by introducing this protecting group and carrying out the reaction followed by removing the protecting group as necessary, or converting it to a desired group. The resulting compounds of the present invention can be identified, and their composition or purity can be analyzed, by standard analytical technologies such as elementary analysis, NMR, mass spectroscopy, or IR analysis.

Raw materials and reagents used to produce the compounds of the present invention can be purchased from commercial suppliers, or can be synthesized according to methods described in the literature.

In the present invention, examples of anemia include nephrogenic anemia, anemia of prematurity, anemia incidental to chronic diseases, anemia incidental to cancer chemotherapy, cancerous anemia, inflammation-associated anemia, and anemia incidental to congestive heart failure. Examples of the anemia incidental to chronic diseases include anemia incidental to chronic kidney diseases, and examples of the chronic kidney diseases include chronic renal failure. Further, the patient to whom the compound of the present invention is administered can be a patient who does or does not receive dialysis.

EFFECTS OF INVENTION

The compounds of the present invention or pharmacologically acceptable salts thereof demonstrate a superior EPO production-enhancing activity in an assay system using Hep3B cells, and have superior safety. Specifically, EPO production can be enhanced by administering a pharmaceutical composition containing a compound of the present invention or a pharmacologically acceptable salt thereof to a mammal (such as a human, cow, horse, or pig) or bird (such as a chicken). Thus, a pharmaceutical composition containing a compound of the present invention or a pharmacologically acceptable salt thereof can be used for the prophylaxis and/or treatment of, for example, diseases caused by decreased EPO, or diseases or pathological conditions in which EPO is decreased such as ischemic cerebrovascular disease, or for autologous transfusion in patients scheduled to undergo surgery. Examples of diseases caused by decreased EPO include anemia, and particularly nephrogenic anemia (dialysis stage, conservation stage), anemia of prematurity, anemia incidental to chronic diseases, anemia incidental to cancer chemotherapy, cancerous anemia, inflammation-associated anemia, and anemia incidental to congestive heart failure.

DESCRIPTION OF EMBODIMENTS

The following provides examples of representative methods for producing the compounds of the present invention. Furthermore, the production methods of the present invention are not limited to the examples shown below.

Compounds having the general formula (1) of the present invention can be obtained according to methods described below.

(Production Method 1)

Production Method 1 is a method for producing compound (1a) which is compound (1) of the present invention wherein L is a group represented by the formula —NHCO— and X is a nitrogen atom.

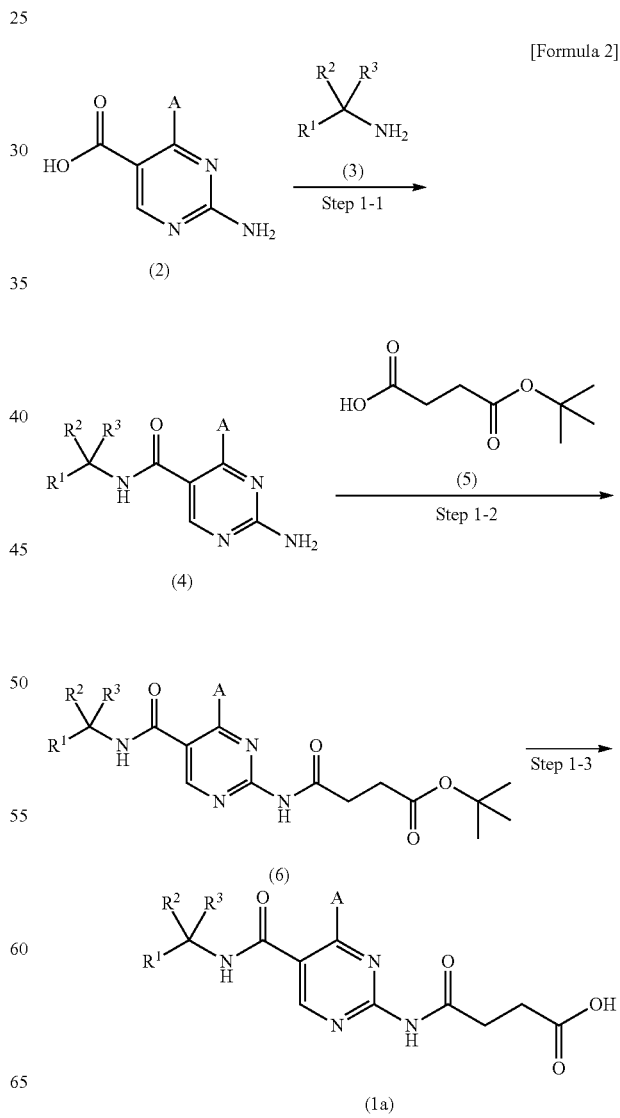

In the above formulae, $R^1$, $R^2$, $R^3$, and A have the same meanings as previously defined.

(Step 1-1)

This step is a step for producing compound (4) from compound (2) and compound (3) in the presence of a condensation agent and a base in a reaction inert solvent.

Although there are no particular limitations on the solvent used provided it does not inhibit the reaction and dissolves the starting material to a certain degree, preferred examples include: halogenated hydrocarbons such as dichloromethane, chloroform, carbon tetrachloride, 1,2-dichloroethane, chlorobenzene, and dichlorobenzene; ethers such as diethyl ether, diisopropyl ether, tetrahydrofuran, 1,4-dioxane, dimethoxyethane, and tert-butyl methyl ether; alcohols such as methanol, ethanol, n-propanol, isopropanol, n-butanol, isobutanol, tert-butanol, isoamyl alcohol, octanol, cyclohexanol, 2-methoxyethanol, diethylene glycol, and glycerin; amides such as N,N-dimethylformamide, N,N-dimethylacetamide, N-methyl-2-pyrrolidinone, and hexamethylphosphorotriamide; water; and mixed solvents thereof, and N,N-dimethylformamide is more preferred.

Although there are no particular limitations on the condensation agent used provided it is used as a condensation agent that forms an amide bond, preferred examples include 2-(1H-7-azabenzotriazol-1-yl)-1,1,3,3-tetramethyluronium hexafluorophosphate, 2-(1H-benzotriazol-1-yl)-1,1,3,3-tetramethyluronium hexafluorophosphate, (1H-benzotriazol-1-yloxy)tripyrrolidinophosphonium hexafluorophosphate, 1,1'-carbonyldiimidazole, N,N'-diisopropylcarbodiimide, 1-ethyl-3-(3-dimethylaminopropyl)carbodiimide hydrochloride, and 4-(4,6-dimethoxy-1,3,5-triazin-2-yl)-4-methylmorpholinium chloride, and 2-(1H-7-azabenzotriazol-1-yl)-1,1,3,3-tetramethyluronium hexafluorophosphate is more preferred.

Although there are no particular limitations on the base used provided it is used as a base in conventional reactions, preferred examples include: organic bases such as triethylamine, N,N-diisopropylethylamine, N-methylmorpholine, pyridine, and 4-(N,N-dimethylamino)pyridine; and inorganic bases such as potassium carbonate, cesium carbonate, and sodium hydrogencarbonate. Organic bases are more preferred, and triethylamine is even more preferred.

Varying according to the raw material compounds, reagents and the like, the reaction temperature is normally 0° C. to 100° C., preferably 20° C. to 40° C. Varying according to the raw material compounds, reagents and the like, the reaction time is normally 2 hours to 48 hours, preferably 4 hours to 24 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified, if necessary, using a conventional method, for example, recrystallization, reprecipitation, or silica gel column chromatography.

(Step 1-2)

This step is a step for producing compound (6) from compound (4) and compound (5) in the presence of a condensation agent and a base in a reaction inert solvent.

Although there are no particular limitations on the solvent used provided it does not inhibit the reaction and dissolves the starting material to a certain degree, preferred examples include: halogenated hydrocarbons such as dichloromethane, chloroform, carbon tetrachloride, 1,2-dichloroethane, chlorobenzene, and dichlorobenzene; ethers such as diethyl ether, diisopropyl ether, tetrahydrofuran, 1,4-dioxane, dimethoxyethane, and tert-butyl methyl ether; alcohols such as methanol, ethanol, n-propanol, isopropanol, n-butanol, isobutanol, tert-butanol, isoamyl alcohol, octanol, cyclohexanol, 2-methoxyethanol, diethylene glycol, and glycerin; amides such as N,N-dimethylformamide, N,N-dimethylacetamide, N-methyl-2-pyrrolidinone, and hexamethylphosphorotriamide; water; and mixed solvents thereof, and N,N-dimethylformamide is more preferred.

Although there are no particular limitations on the condensation agent used provided it is used as a condensation agent that forms an amide bond, preferred examples include 2-(1H-7-azabenzotriazol-1-yl)-1,1,3,3-tetramethyluronium hexafluorophosphate, 2-(1H-benzotriazol-1-yl)-1,1,3,3-tetramethyluronium hexafluorophosphate, (1H-benzotriazol-1-yloxy)tripyrrolidinophosphonium hexafluorophosphate, 1,1'-carbonyldiimidazole, N,N'-diisopropylcarbodiimide, 1-ethyl-3-(3-dimethylaminopropyl)carbodiimide hydrochloride, and 4-(4,6-dimethoxy-1,3,5-triazin-2-yl)-4-methylmorpholinium chloride, and 2-(1H-7-azabenzotriazol-1-yl)-1,1,3,3-tetramethyluronium hexafluorophosphate is more preferred.

Although there are no particular limitations on the base used provided it is used as a base in conventional reactions, preferred examples include: organic bases such as triethylamine, N,N-diisopropylethylamine, N-methylmorpholine, pyridine, and 4-(N,N-dimethylamino)pyridine; and inorganic bases such as potassium carbonate, cesium carbonate, and sodium hydrogencarbonate. Organic bases are more preferred, and N,N-diisopropylethylamine is even more preferred.

Varying according to the raw material compounds, reagents and the like, the reaction temperature is normally 20° C. to 150° C., preferably 60° C. to 120° C. Varying according to the raw material compounds, reagents and the like, the reaction time is normally 1 hour to 60 hours, preferably 3 hours to 48 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified, if necessary, using a conventional method, for example, recrystallization, reprecipitation, or silica gel column chromatography.

(Step 1-3)

This step is a step for producing compound (1a) of the present invention from compound (6) in the presence of an acid in a reaction inert solvent.

Although there are no particular limitations on the solvent used provided it does not inhibit the reaction and dissolves the starting material to a certain degree, preferred examples include: aromatic hydrocarbons such as benzene, toluene, and xylene; aliphatic hydrocarbons such as pentane, hexane, and cyclohexane; halogenated hydrocarbons such as dichloromethane, chloroform, carbon tetrachloride, 1,2-dichloroethane, chlorobenzene, and dichlorobenzene; esters such as ethyl formate, ethyl acetate, propyl acetate, butyl acetate, and diethyl carbonate; ethers such as diethyl ether, diisopropyl ether, tetrahydrofuran, 1,4-dioxane, dimethoxyethane, and tert-butyl methyl ether; water; and mixed solvents thereof, and dichloromethane is more preferred.

Examples of the acid used include those described in, for example, Greene and Wuts, "Protective Groups in Organic Synthesis", 3rd ed., 1999, and trifluoroacetic acid is preferred.

Varying according to the raw material compounds, reagents and the like, the reaction temperature is normally −50° C. to 100° C., preferably 0° C. to 50° C. Varying according to the raw material compounds, reagents and the like, the reaction time is normally 15 minutes to 30 hours, preferably 30 minutes to 20 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified, if necessary, using a conventional method, for example, recrystallization, reprecipitation, or silica gel column chromatography.

(Production Method 2)

Production Method 2 is a method for producing compound (1b) which is compound (1) of the present invention wherein A is a hydroxy group, L is a group represented by the formula —NHCO—, and X is a group represented by the formula =CH—.

[Formula 3]

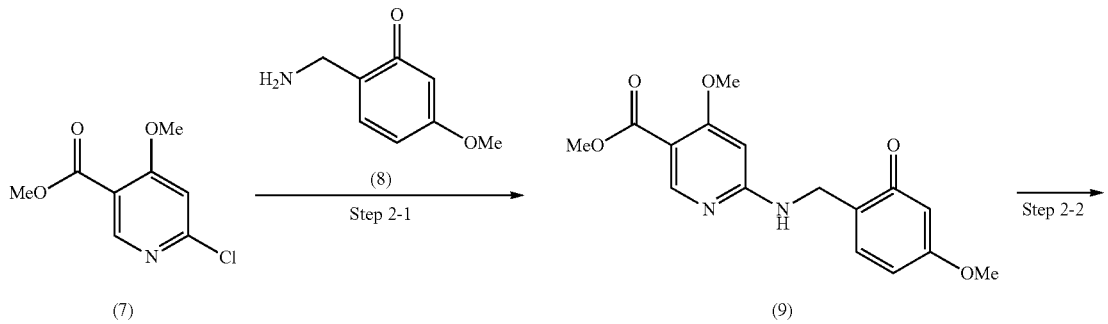

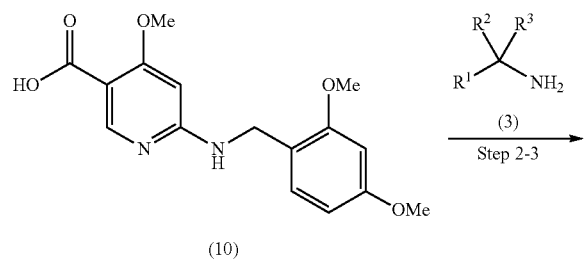

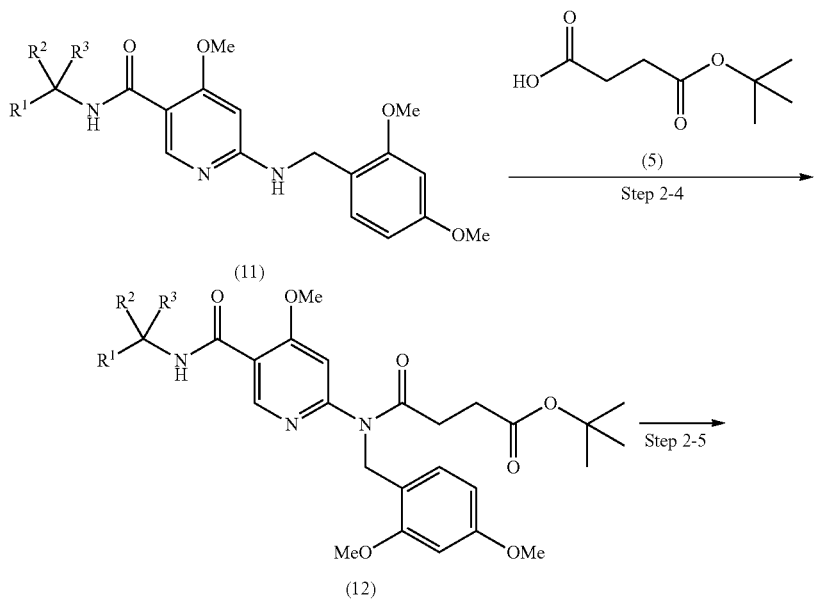

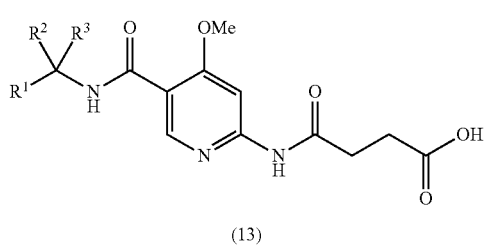

(13)

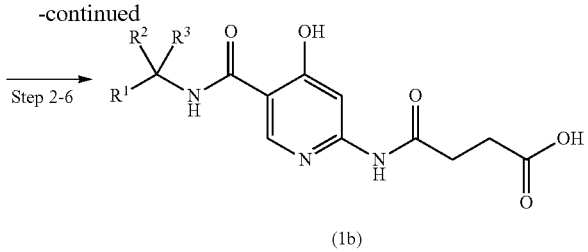

(1b)

In the above formulae, $R^1$, $R^2$, and $R^3$ have the same meanings as previously defined.
(Step 2-1)

This step is a step for producing compound (9) from compound (7) and compound (8) in the presence of a base in a reaction inert solvent.

Although there are no particular limitations on the solvent used provided it does not inhibit the reaction and dissolves the starting material to a certain degree, preferred examples include: aromatic hydrocarbons such as benzene, toluene, and xylene; ethers such as diethyl ether, diisopropyl ether, tetrahydrofuran, 1,4-dioxane, dimethoxyethane, and tert-butyl methyl ether; amides such as N,N-dimethylformamide, N,N-dimethylacetamide, N-methyl-2-pyrrolidinone, and hexamethylphosphorotriamide; and mixed solvents thereof, and N,N-dimethylacetamide is more preferred.

Although there are no particular limitations on the base used provided it is used as a base in conventional reactions, preferred examples include: organic bases such as triethylamine, N,N-diisopropylethylamine, N-methylmorpholine, pyridine, and 4-(N,N-dimethylamino)pyridine; and inorganic bases such as sodium carbonate, potassium carbonate, cesium carbonate, sodium hydrogencarbonate, sodium tert-butoxide, and potassium tert-butoxide. Inorganic bases are more preferred, and potassium carbonate is even more preferred.

Varying according to the raw material compounds, reagents and the like, the reaction temperature is normally 20° C. to 200° C., preferably 80° C. to 150° C. Varying according to the raw material compounds, reagents and the like, the reaction time is normally 4 hours to 48 hours, preferably 8 hours to 24 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified, if necessary, using a conventional method, for example, recrystallization, reprecipitation, or silica gel column chromatography.
(Step 2-2)

This step is a step for producing compound (10) from compound (9) in the presence of a base in a reaction inert solvent.

Although there are no particular limitations on the solvent used provided it does not inhibit the reaction and dissolves the starting material to a certain degree, preferred examples include: ethers such as diethyl ether, diisopropyl ether, tetrahydrofuran, dioxane, dimethoxyethane, and tert-butyl methyl ether; alcohols such as methanol, ethanol, n-propanol, isopropanol, n-butanol, isobutanol, tert-butanol, isoamyl alcohol, octanol, cyclohexanol, 2-methoxyethanol, diethylene glycol, and glycerin; water; and mixed solvents thereof, and a mixed solvent of tetrahydrofuran, methanol, and water is more preferred.

Examples of the base used include bases described in, for example, Greene and Wuts, "Protective Groups in Organic Synthesis", 3rd ed., 1999, and potassium hydroxide or sodium hydroxide is preferred.

Varying according to the raw material compounds, reagents and the like, the reaction temperature is normally 0° C. to 100° C., preferably 20° C. to 60° C. Varying according to the raw material compounds, reagents and the like, the reaction time is normally 30 minutes to 24 hours, preferably 1 hour to 18 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified, if necessary, using a conventional method, for example, recrystallization, reprecipitation, or silica gel column chromatography.
(Step 2-3)

This step is a step for producing compound (11) from compound (3) and compound (10) in the same way as in Step 1-1.
(Step 2-4)

This step is a step for producing compound (12) from compound (5) and compound (11) in the same way as in Step 1-2.
(Step 2-5)

This step is a step for producing compound (13) from compound (12) in the same way as in Step 1-3.
(Step 2-6)

This step is a step for producing compound (1b) of the present invention from compound (13) in the presence of a Lewis acid in a reaction inert solvent.

Although there are no particular limitations on the solvent used provided it does not inhibit the reaction and dissolves the starting material to a certain degree, preferred examples include: halogenated hydrocarbons such as dichloromethane, chloroform, carbon tetrachloride, 1,2-dichloroethane, chlorobenzene, and dichlorobenzene; and nitriles such as acetonitrile, and dichloromethane is more preferred.

Although there are no particular limitations on the Lewis acid used provided it is used in known methods, preferred examples include boron tribromide, boron trichloride, and aluminum tribromide, and boron tribromide is more preferred.

Varying according to the raw material compounds, reagents and the like, the reaction temperature is normally −78° C. to 50° C., preferably 30° C. to 40° C. Varying according to the raw material compounds, reagents and the like, the reaction time is normally 2 hours to 12 hours, preferably 4 hours to 8 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified, if necessary, using a conventional method, for example, recrystallization, reprecipitation, or silica gel column chromatography.

(Production Method 3)

Production Method 3 is a method for producing compound (1c) which is compound (1) of the present invention wherein A is a hydrogen atom, L is a group represented by the formula —OCH$_2$—, and X is a group represented by the formula =CH—.

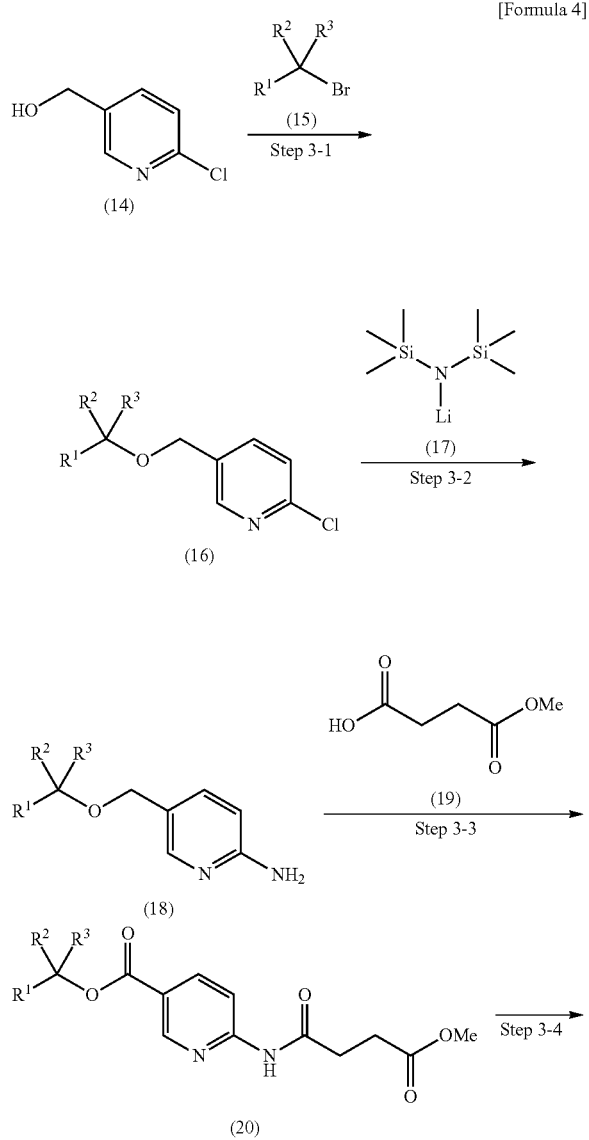

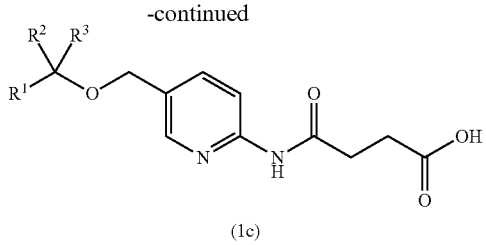

In the above formulae, $R^1$, $R^2$, and $R^3$ have the same meanings as previously defined.

(Step 3-1)

This step is a step for producing compound (16) from compound (14) and compound (15) in the presence of a base in a reaction inert solvent.

Although there are no particular limitations on the solvent used provided it does not inhibit the reaction and dissolves the starting material to a certain degree, preferred examples include: aromatic hydrocarbons such as benzene, toluene, and xylene; ethers such as diethyl ether, diisopropyl ether, tetrahydrofuran, 1,4-dioxane, dimethoxyethane, and tert-butyl methyl ether; amides such as N,N-dimethylformamide, N,N-dimethylacetamide, N-methyl-2-pyrrolidinone, and hexamethylphosphorotriamide; and mixed solvents thereof, and tetrahydrofuran is more preferred.

Although there are no particular limitations on the base used provided it is used in known methods, preferred examples include lithium hexamethyldisilazide, sodium hexamethyldisilazide, lithium diisopropylamide, sodium hydride, sodium tert-butoxide, and potassium tert-butoxide, and sodium hydride is more preferred.

Varying according to the raw material compounds, reagents and the like, the reaction temperature is normally 0° C. to 100° C., preferably 20° C. to 80° C. Varying according to the raw material compounds, reagents and the like, the reaction time is normally 1 hour to 24 hours, preferably 2 hours to 18 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified, if necessary, using a conventional method, for example, recrystallization, reprecipitation, or silica gel column chromatography.

(Step 3-2)

This step is a step for producing compound (18) from compound (16) and compound (17) in the presence of a palladium catalyst and a ligand in a reaction inert solvent.

Although there are no particular limitations on the solvent used provided it does not inhibit the reaction and dissolves the starting material to a certain degree, preferred examples include: aromatic hydrocarbons such as benzene, toluene, and xylene; ethers such as diethyl ether, diisopropyl ether, tetrahydrofuran, dioxane, dimethoxyethane, and tert-butyl methyl ether; amides such as N,N-dimethylformamide, N,N-dimethylacetamide, N-methyl-2-pyrrolidinone, and hexamethylphosphorotriamide; water; and mixed solvents thereof, and tetrahydrofuran is more preferred.

Although there are no particular limitations on the palladium catalyst used provided it is used in known methods, preferred examples include tetrakis(triphenylphosphine) palladium, bis(dibenzylideneacetone) palladium, tris(dibenzylideneacetone)dipalladium, bis(triphenylphosphine)dichloropalladium, [1,1'-bis(diphenylphosphino)ferrocene]dichloropalladium, bis(2,4-pentanedionato) palladium, and palladium acetate, and tris(dibenzylideneacetone)dipalladium is more preferred.

Although there are no particular limitations on the ligand used provided it is used in known methods, preferred examples include triphenylphosphine, 2-(dicyclohexylphosphino)biphenyl, 2-(di-tert-butylphosphino)biphenyl, 1,4-bis(diphenylphosphino)butane, 1,1'-bis(diphenylphosphino)ferrocene, and 2,2'-bis(diphenylphosphino)-1,1'-binaphthyl, and 2-(dicyclohexylphosphino)biphenyl is more preferred.

Varying according to the raw material compounds, reagents and the like, the reaction temperature is normally 20° C. to 100° C., preferably 50° C. to 80° C. Varying according to the raw material compounds, reagents and the like, the reaction time is normally 3 hours to 48 hours, preferably 6 hours to 24 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified, if necessary, using a conventional method, for example, recrystallization, reprecipitation, or silica gel column chromatography.

(Step 3-3)

This step is a step for producing compound (20) from compound (18) and compound (19) in the presence of a condensation agent and a base in a reaction inert solvent.

Although there are no particular limitations on the solvent used provided it does not inhibit the reaction and dissolves the starting material to a certain degree, preferred examples include: halogenated hydrocarbons such as dichloromethane, chloroform, carbon tetrachloride, 1,2-dichloroethane, chlorobenzene, and dichlorobenzene; ethers such as diethyl ether, diisopropyl ether, tetrahydrofuran, 1,4-dioxane, dimethoxyethane, and tert-butyl methyl ether; alcohols such as methanol, ethanol, n-propanol, isopropanol, n-butanol, isobutanol, tert-butanol, isoamyl alcohol, octanol, cyclohexanol, 2-methoxyethanol, diethylene glycol, and glycerin; amides such as N,N-dimethylformamide, N,N-dimethylacetamide, N-methyl-2-pyrrolidinone, and hexamethylphosphorotriamide; water; and mixed solvents thereof, and N,N-dimethylformamide is more preferred.

Although there are no particular limitations on the condensation agent used provided it is used as a condensation agent that forms an amide bond, preferred examples include 2-(1H-7-azabenzotriazol-1-yl)-1,1,3,3-tetramethyluronium hexafluorophosphate, 2-(1H-benzotriazol-1-yl)-1,1,3,3-tetramethyluronium hexafluorophosphate, (1H-benzotriazol-1-yloxy)tripyrrolidinophosphonium hexafluorophosphate, 1,1'-carbonyldiimidazole, N,N'-diisopropylcarbodiimide, 1-ethyl-3-(3-dimethylaminopropyl)carbodiimide hydrochloride, and 4-(4,6-dimethoxy-1,3,5-triazin-2-yl)-4-methylmorpholinium chloride, and 2-(1H-7-azabenzotriazol-1-yl)-1,1,3,3-tetramethyluronium hexafluorophosphate is more preferred.

Although there are no particular limitations on the base used provided it is used as a base in conventional reactions, preferred examples include: organic bases such as triethylamine, N,N-diisopropylethylamine, N-methylmorpholine, pyridine, and 4-(N,N-dimethylamino)pyridine; and inorganic bases such as potassium carbonate, cesium carbonate, and sodium hydrogencarbonate. Organic bases are more preferred, and N,N-diisopropylethylamine is even more preferred.

Varying according to the raw material compounds, reagents and the like, the reaction temperature is normally 20° C. to 150° C., preferably 60° C. to 120° C. Varying according to the raw material compounds, reagents and the like, the reaction time is normally 1 hour to 24 hours, preferably 2 hours to 18 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified, if necessary, using a conventional method, for example, recrystallization, reprecipitation, or silica gel column chromatography.

(Step 3-4)

This step is a step for producing compound (1c) of the present invention from compound (20) in the same way as in Step 2-2.

The reaction products obtained according to each of the aforementioned steps are isolated and purified as non-solvates, salts thereof or various types of solvates such as hydrates. Salts thereof can be produced according to a conventional method. Isolation or purification is carried out by applying conventional methods such as extraction, concentration, distillation, crystallization, filtration, recrystallization, or various types of chromatography.

Each type of isomer can be isolated in accordance with conventional methods by utilizing differences in physicochemical properties between isomers. For example, optical isomers can be separated by common optical resolution methods (e.g., fractional crystallization, chromatography, etc.). In addition, optical isomers can also be produced from suitable optically active raw material compounds.

A formulation containing a compound of the present invention as an active ingredient is prepared using additives such as a carrier and an excipient used for conventional formulations. Administration of a compound of the present invention may be oral administration in the form of tablets, pills, capsules, granules, powders, liquids, or the like, or parenteral administration in the form of injections (e.g., intravenous injection and intramuscular injection), suppositories, transcutaneous agents, nasal agents, inhalants, or the like. Dosage and frequency of administration of a compound of the present invention are suitably determined on an individual basis in consideration of such factors as symptoms and age or gender of the recipient. The dosage is normally 0.001 to 100 mg/kg per administration for a human adult in the case of oral administration, and in the case of intravenous administration, the dosage is normally 0.0001 to 10 mg/kg per administration for a human adult. The frequency of administration is normally 1 to 6 times a day, or once a day to once in 7 days. It is also preferred that administration to a patient who receives dialysis should be carried out once before or after each dialysis (preferably before dialysis) that the patient receives.

Solid formulations for oral administration according to the present invention may be tablets, powders, granules, or the like. Such formulations are produced in accordance with a conventional method by mixing one or more active substances with an inert excipient, lubricant, disintegrant, or dissolution aid. The excipient may be, for example, lactose, mannitol, or glucose. The lubricant may be, for example, magnesium stearate. The disintegrant may be, for example, sodium carboxymethyl starch. The tablets or pills may be provided with a sugar coating, or a gastric or enteric coating as necessary.

Liquid formulations for oral administration may be pharmaceutically acceptable emulsions, liquids, suspensions, syrups, elixirs, or the like. Such formulations may contain commonly used inert solvents (e.g., purified water or ethanol), and may further contain solubilizers, wetting agents, suspending agents, sweeteners, corrigents, fragrances, or preservatives.

Injections for parenteral administration may be sterile aqueous or non-aqueous liquid formulations, suspensions, or emulsions. Aqueous solvents for injections may be, for example, distilled water or physiological saline. Non-aqueous solvents for injections may be, for example, propylene glycol, polyethylene glycol, vegetable oils such as olive oil, alcohols such as ethanol, or Polysorbate 80 (Japanese Pharmacopoeia name). Such formulations may further contain isotonic agents, preservatives, wetting agents, emulsifiers, dispersants, stabilizers, or dissolution aids. These formulations may be sterilized, for example, by passing through a bacteria-retaining filter, incorporation of a bactericide, or irradiation. Further, it is also possible to use, as these formulations, compositions obtained by dissolving or suspending a sterile solid composition in sterile water or a solvent for injection prior to use.

EXAMPLES

Although the following provides examples and test examples to explain the present invention in more detail, the scope of the present invention is not limited thereto.

Example 1

4-({5-[(2,4-Dichlorophenyl)methylcarbamoyl]-4-hydroxypyrimidin-2-yl}amino)-4-oxobutanoic acid

[Formula 5]

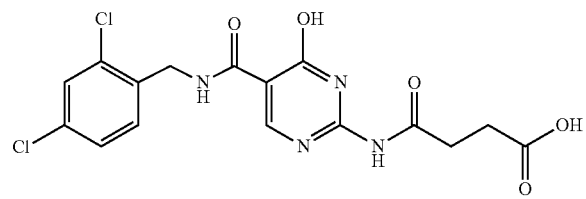

(1) 2-Amino-N-[(2,4-dichlorophenyl)methyl]-4-hydroxypyrimidine-5-carboxamide

[Formula 6]

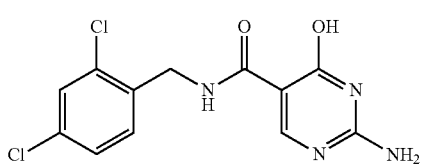

To a suspension of 2-amino-4-hydroxypyrimidine-5-carboxylic acid (311 mg), (2,4-dichlorophenyl)methanamine (353 mg), and triethylamine (2.8 mL) in N,N-dimethylformamide (8 mL), 2-(1H-7-azabenzotriazol-1-yl)-1,1,3,3-tetramethyluronium hexafluorophosphate (839 mg) was added at room temperature, and the mixture was stirred for 90 minutes. 2,4-Dichlorobenzylamine (353 mg) and 2-(1H-7-azabenzotriazol-1-yl)-1,1,3,3-tetramethyluronium hexafluorophosphate (839 mg) were added thereto, and the mixture was stirred for 12 hours. A saturated aqueous ammonium chloride solution was added to the reaction solution, and the mixture was stirred for 1 hour and then filtered. The product collected by filtration was washed with water, dried under reduced pressure, and then suspended in ethyl acetate. This suspension was shaken for 1 hour in an ultrasonic bath and then filtered. The obtained product collected by filtration was dried under reduced pressure to obtain the title compound (326 mg).

$^1$H-NMR (400 MHz, DMSO-$D_6$) δ: 9.31 (1H, brs), 8.39 (1H, s), 7.62 (1H, d, J=2 Hz), 7.41 (1H, dd, J=8 Hz, 2 Hz), 7.33 (1H, d, J=8 Hz), 4.50 (2H, d, J=6 Hz).

(2) Tert-butyl 4-({5-[(2,4-dichlorophenyl)methylcarbamoyl]-4-hydroxypyrimidin-2-yl}amino)-4-oxobutanoate

[Formula 7]

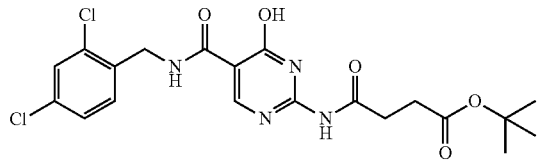

To a solution of 2-amino-N-[(2,4-dichlorophenyl)methyl]-4-hydroxypyrimidine-5-carboxamide (317 mg), 4-tert-butoxy-4-oxobutanoic acid (529 mg), and N,N-diisopropylethylamine (1.06 mL) in N,N-dimethylformamide (8 mL), 2-(1H-7-azabenzotriazol-1-yl)-1,1,3,3-tetramethyluronium hexafluorophosphate (1160 mg) was added at room temperature, and the mixture was stirred at 80° C. for 5 hours. The reaction solution was cooled to room temperature. Then, a saturated aqueous ammonium chloride solution was added thereto, and the mixture was stirred for 10 minutes. The resulting suspension was filtered. The product collected by filtration was washed with water and dried under reduced pressure to obtain the title compound (430 mg).

MS m/z: 469 (M+H)$^+$.

(3) 4-({5-[(2,4-Dichlorophenyl)methylcarbamoyl]-4-hydroxypyrimidin-2-yl}amino)-4-oxobutanoic acid A solution of tert-butyl 4-({5-[(2,4-dichlorophenyl)methylcarbamoyl]-4-hydroxypyrimidin-2-yl}amino)-4-oxobutanoate (425 mg) in trifluoroacetic acid (3 mL) was left standing at room temperature for 30 minutes. Ether (60 mL) was added to the reaction solution, and the resulting suspension was filtered. The product collected by filtration was washed with ether, dried under reduced pressure, and then purified by reverse phase high performance liquid chromatography (acetonitrile/water, containing 0.1% formic acid) to obtain the title compound (144 mg).

MS m/z: 413 (M+H)$^+$;

$^1$H-NMR (400 MHz, DMSO-D$_6$) δ: 8.49 (1H, brs), 7.63 (1H, d, J=2 Hz), 7.42 (1H, dd, J=8 Hz, 2 Hz), 7.36 (1H, d, J=8 Hz), 4.54 (2H, d, J=6 Hz), 2.73-2.70 (2H, m), 2.56-2.53 (2H, m).

Example 2

4-({5-[(2,4-Difluorophenyl)methylcarbamoyl]-4-hydroxypyrimidin-2-yl}amino)-4-oxobutanoic acid

[Formula 8]

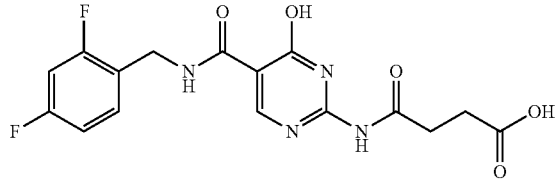

The title compound was obtained in accordance with the method of Example 1, but using (2,4-difluorophenyl)methanamine instead of (2,4-dichlorophenyl)methanamine.

MS m/z: 381 (M+H)$^+$;

$^1$H-NMR (400 MHz, DMSO-D$_6$) δ: 9.22-8.38 (1H, brm), 7.40 (1H, td, J=9 Hz, 7 Hz), 7.24 (1H, ddd, J=11 Hz, 9 Hz, 3 Hz), 7.06 (1H, tdd, J=9 Hz, 3 Hz, 1 Hz), 4.50 (2H, d, J=6 Hz), 2.73-2.69 (2H, m), 2.56-2.53 (2H, m).

Example 3

4-({5-[(2-Chloro-4-fluorophenyl)methylcarbamoyl]-4-hydroxypyrimidin-2-yl}amino)-4-oxobutanoic acid

[Formula 9]

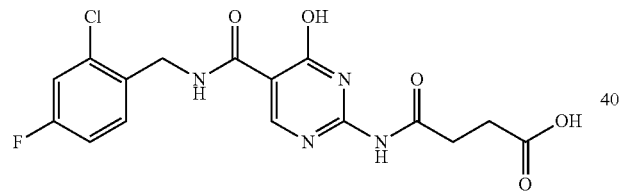

The title compound was obtained in accordance with the method of Example 1, but using (2-chloro-4-fluorophenyl)methanamine instead of (2,4-dichlorophenyl)methanamine.

MS m/z: 397 (M+H)$^+$;

$^1$H-NMR (400 MHz, DMSO-D$_6$) δ: 8.61-8.33 (1H, brm), 7.46 (1H, dd, J=9 Hz, 3 Hz), 7.41 (1H, dd, J=9 Hz, 6 Hz), 7.21 (1H, td, J=9 Hz, 3 Hz), 4.53 (2H, d, J=6 Hz), 2.77-2.65 (2H, m), 2.56-2.53 (2H, m).

Example 4

4-{[4-Hydroxy-5-(p-tolylmethylcarbamoyl)pyrimidin-2-yl]amino}-4-oxobutanoic acid

[Formula 10]

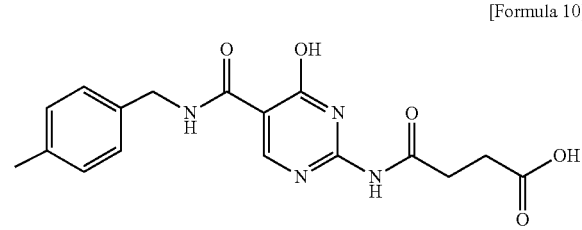

The title compound was obtained in accordance with the method of Example 1, but using p-tolylmethanamine instead of (2,4-dichlorophenyl)methanamine.

MS m/z: 359 (M+H)$^+$;

$^1$H-NMR (400 MHz, DMSO-d$_6$) δ: 8.36 (1H, brs), 7.19 (2H, d, J=8 Hz), 7.14 (2H, d, J=8 Hz), 4.45 (2H, d, J=6 Hz), 2.73-2.67 (2H, m), 2.56-2.51 (2H, m), 2.28 (3H, s).

Example 5

4-({5-[(4-Fluoro-3-phenylphenyl)methylcarbamoyl]-4-hydroxypyrimidin-2-yl}amino)-4-oxobutanoic acid

[Formula 11]

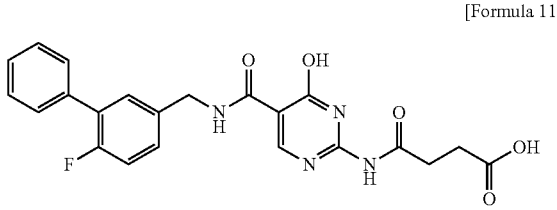

(1) (4-Fluoro-3-phenylphenyl)methanamine

[Formula 12]

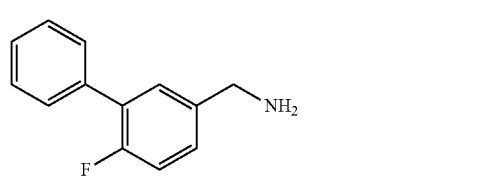

To a solution of 5-cyano-2-fluorobiphenyl (1.96 g) in tetrahydrofuran (35 mL), a solution of borane in tetrahydrofuran (1 M, 35 mL) was added dropwise at room temperature, and the mixture was stirred for 22 hours. Hydrochloric acid (1 M, 7 mL) was gradually added dropwise to the reaction solution, and the mixture was stirred for 2 hours. A 2 M aqueous sodium hydroxide solution was added thereto for separation into organic and aqueous layers. The aqueous layer was subjected to extraction with ethyl acetate. All the organic layers were combined, dried over anhydrous sodium sulfate, and then filtered, and the filtrate was concentrated under reduced pressure. The obtained residue was purified by chromatography on a silica gel column (Biotage Ltd., elution solvent: hexane/ethyl acetate) to obtain the title compound (1.25 g).

$^1$H-NMR (400 MHz, CDCl$_3$) δ: 7.57-7.54 (2H, m), 7.47-7.42 (2H, m), 7.40-7.37 (2H, m), 7.26-7.25 (1H, m), 7.12 (1H, dd, J=10 Hz, 8 Hz), 3.90 (2H, s).

(2) 4-({5-[(4-Fluoro-3-phenylphenyl)methylcarbamoyl]-4-hydroxypyrimidin-2-yl}amino)-4-oxobutanoic acid The title compound was obtained in accordance with the method of Example 1, but using (4-fluoro-3-phenylphenyl)methanamine instead of (2,4-dichlorophenyl)methanamine.

MS m/z: 439 (M+H)$^+$;
$^1$H-NMR (400 MHz, DMSO-D$_6$) δ: 9.29-8.61 (1H, brm), 7.54-7.50 (5H, m), 7.45-7.41 (1H, m), 7.39-7.35 (1H, m), 7.29 (1H, dd, J=11 Hz, 8 Hz), 4.55 (2H, d, J=6 Hz), 2.74-2.71 (2H, m), 2.58-2.55 (2H, m).

Example 6

4-({4-Hydroxy-5-[(3-phenylphenyl)methylcarbamoyl]pyrimidin-2-yl}amino)-4-oxobutanoic acid

[Formula 13]

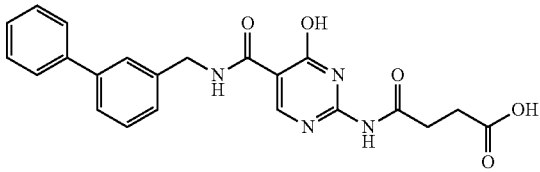

(1) Tert-butyl 4-({4-hydroxy-5-[(3-phenylphenyl)methylcarbamoyl]pyrimidin-2-yl}amino)-4-oxobutanoate

[Formula 14]

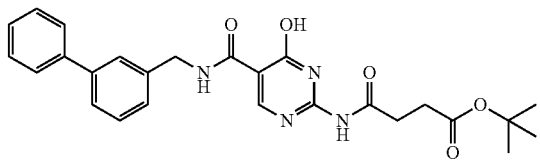

The title compound was obtained in accordance with the method of Examples 1(1) and 1(2), but using (3-phenylphenyl)methanamine instead of (2,4-dichlorophenyl)methanamine.

$^1$H-NMR (400 MHz, CDCl$_3$) δ: 9.32 (1H, brs), 8.85 (1H, brs), 7.59-7.31 (10H, m), 4.69 (2H, d, J=6 Hz), 2.72-2.63 (4H, m), 1.45 (9H, s).

(2) 4-({4-Hydroxy-5-[(3-phenylphenyl)methylcarbamoyl]pyrimidin-2-yl}amino)-4-oxobutanoic acid A solution of tert-butyl 4-({4-hydroxy-5-[(3-phenylphenyl)methylcarbamoyl]pyrimidin-2-yl}amino)-4-oxobutanoate (110 mg) in trifluoroacetic acid (1.5 mL) was left standing at room temperature for 1 hour. Ether (30 mL) was added to the reaction solution, and the resulting suspension was filtered. The product collected by filtration was washed with ether and hexane and dried under reduced pressure to obtain the title compound (88 mg).

MS m/z: 421 (M+H)$^+$;
$^1$H-NMR (400 MHz, DMSO-D$_6$) δ: 8.53 (1H, brs), 7.65-7.30 (9H, m), 4.57 (2H, d, J=6 Hz), 2.72-2.69 (2H, m), 2.56-2.53 (2H, m).

Example 7

4-[(5-{[4-(2-Cyanophenyl)phenyl]methylcarbamoyl}-4-hydroxypyrimidin-2-yl)amino]-4-oxobutanoic acid

[Formula 15]

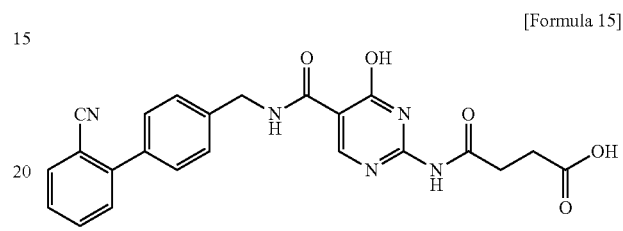

The title compound was obtained in accordance with the method of Example 6, but using 2-[4-(aminomethyl)phenyl]benzonitrile instead of (3-phenylphenyl)methanamine.

MS m/z: 446 (M+H)$^+$;
$^1$H-NMR (400 MHz, DMSO-D$_6$) δ: 8.64 (1H, brs), 7.95 (1H, dd, J=8 Hz, 1 Hz), 7.79 (1H, td, J=8 Hz, 1 Hz), 7.63-7.54 (4H, m), 7.46 (2H, d, J=8 Hz), 4.59 (2H, d, J=6 Hz), 2.74-2.70 (2H, m), 2.56-2.53 (2H, m).

Example 8

4-[(5-{[3-(2-Cyanophenyl)phenyl]methylcarbamoyl}-4-hydroxypyrimidin-2-yl)amino]-4-oxobutanoic acid

[Formula 16]

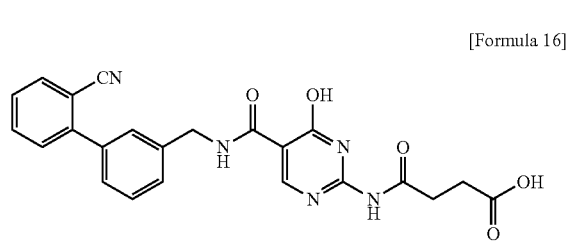 [SMILES: N#Cc1ccccc1-c1cccc(CNC(=O)c2cnc(NC(=O)CCC(=O)O)nc2O)c1]

(1) 2-[3-(Aminomethyl)phenyl]benzonitrile hydrochloride

[Formula 17]

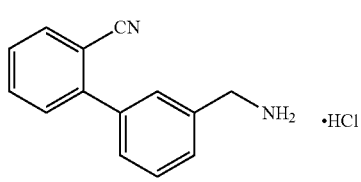

A solution of 2-bromobenzonitrile (1.10 g), 3-aminomethylphenylboronic acid hydrochloride (1.13 g), [1,1'-bis(diphenylphosphino)ferrocene]dichloropalladium-dichloromethane complex (0.10 g), and tripotassium phosphate (5.20 g) in a 4:1 dimethoxyethane-water mixed solvent (60 mL) was stirred at 70° C. for 3 hours. 2-Bromobenzonitrile (0.070 g) and [1,1'-bis(diphenylphosphino)ferrocene]dichloropalladium-dichloromethane complex (0.10 g) were added thereto, and the mixture was stirred at 70° C. for 2 hours. The reaction solution was cooled to room temperature, filtered through celite, and then separated into organic and aqueous layers. The organic layer was washed with a saturated aqueous sodium hydrogencarbonate solution and saturated saline, dried over anhydrous sodium sulfate, and then filtered, and the filtrate was concentrated under reduced pressure. The obtained residue was purified by chromatography on a silica gel column (Biotage Ltd., elution solvent: dichloromethane/methanol), and a fraction containing the desired compound was concentrated under reduced pressure. The obtained residue was dissolved in ethyl acetate, and concentrated hydrochloric acid was added to the solution. The resulting suspension was filtered, and the product collected by filtration was washed with ethyl acetate and dried under reduced pressure to obtain the title compound (0.483 g).

$^1$H-NMR (400 MHz, DMSO-D$_6$) δ: 8.41 (3H, brs), 7.99 (1H, d, J=8 Hz), 7.86-7.82 (1H, m), 7.71 (1H, s), 7.65-7.59 (5H, m), 4.13 (2H, s).

(2) 4-[(5-{[3-(2-Cyanophenyl)phenyl]methylcarbamoyl}-4-hydroxypyrimidin-2-yl)amino]-4-oxobutanoic acid The title compound was obtained in accordance with the method of Example 6, but using 2-[3-(aminomethyl)phenyl]benzonitrile hydrochloride instead of (3-phenylphenyl)methanamine.

MS m/z: 446 (M+H)$^+$;

$^1$H-NMR (400 MHz, DMSO-D$_6$) δ: 8.62 (1H, brs), 7.95 (1H, dd, J=8 Hz, 1 Hz), 7.80 (1H, td, J=8 Hz, 1 Hz), 7.62-7.57 (2H, m), 7.53-7.43 (4H, m), 4.59 (2H, d, J=6 Hz), 2.73-2.69 (2H, m), 2.56-2.53 (2H, m).

Example 9

4-[(4-Hydroxy-5-{[(6-methoxypyridin-3-yl)(tetrahydro-2H-pyran-4-yl)methyl]carbamoyl}pyrimidin-2-yl)amino]-4-oxobutanoic acid trifluoroacetate

[Formula 18]

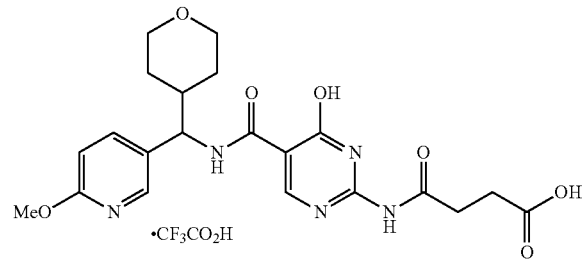

The title compound was obtained in accordance with the method of Example 6, but using 1-(6-methoxypyridin-3-yl)-1-(tetrahydro-2H-pyran-4-yl)methanamine hydrochloride (International Publication No. WO 2011/002623) instead of (3-phenylphenyl)methanamine.

MS m/z: 460 (M+H)$^+$;

$^1$H-NMR (500 MHz, DMSO-d$_6$) δ: 8.53-8.29 (1H, m), 8.09 (1H, d, J=2 Hz), 7.65 (1H, dd, J=9 Hz, 2 Hz), 6.81 (1H, d, J=9 Hz), 4.79 (1H, t, J=8 Hz), 3.90-3.77 (2H, m), 3.82 (3H, s), 3.29-3.17 (2H, m), 2.73-2.68 (2H, m), 2.57-2.52 (2H, m), 2.05-1.94 (1H, m), 1.67-1.59 (1H, m), 1.30-1.17 (3H, m).

Example 10

4-{[4-Hydroxy-5-({1-[6-(4-methoxyphenyl)pyridin-3-yl]-1-methylethyl}carbamoyl)pyrimidin-2-yl]amino}-4-oxobutanoic acid trifluoroacetate

[Formula 19]

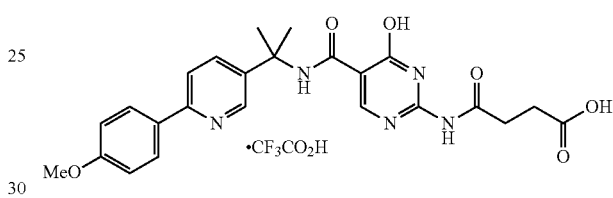

The title compound was obtained in accordance with the method of Example 6, but using 2-[6-(4-methoxyphenyl)pyridin-3-yl]propan-2-amine benzenesulfonate (International Publication No. WO 2011/002624) instead of (3-phenylphenyl)methanamine.

MS m/z: 480 (M+H)$^+$;

$^1$H-NMR (500 MHz, DMSO-d$_6$) δ: 9.38 (1H, brs), 8.62 (1H, s), 8.50 (1H, brs), 8.25 (1H, brs), 8.01 (2H, d, J=9 Hz), 7.90-7.83 (2H, m), 7.06 (2H, d, J=9 Hz), 3.82 (3H, s), 2.77-2.65 (2H, m), 2.58-2.53 (2H, m), 1.72 (6H, s).

Example 11

4-[(4-Hydroxy-5-{[3-(trifluoromethyl)phenyl]methylcarbamoyl}pyrimidin-2-yl)amino]-4-oxobutanoic acid

[Formula 20]

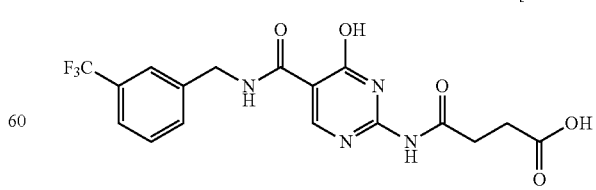

The title compound was obtained in accordance with the method of Example 6, but using [3-(trifluoromethyl)phenyl]methanamine instead of (3-phenylphenyl)methanamine.

MS m/z: 413 (M+H)+;
¹H-NMR (500 MHz, DMSO-d₆) δ: 8.35 (1H, brs), 7.66 (1H, s), 7.63-7.56 (3H, m), 4.59 (2H, d, J=6 Hz), 2.75-2.67 (2H, m), 2.56-2.54 (2H, m).

Example 12

4-({5-[(3-Fluorophenyl)methylcarbamoyl]-4-hydroxypyrimidin-2-yl}amino)-4-oxobutanoic acid

[Formula 21]

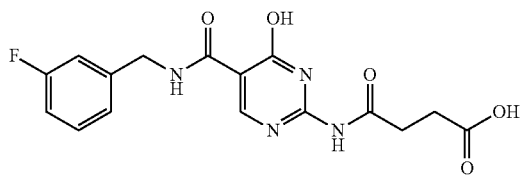

The title compound was obtained in accordance with the method of Example 6, but using (3-fluorophenyl)methanamine instead of (3-phenylphenyl)methanamine.

MS m/z: 363 (M+H)+;
¹H-NMR (500 MHz, DMSO-d₆) δ: 8.35 (1H, brs), 7.38 (1H, dd, J=14 Hz, 7 Hz), 7.16-7.06 (3H, m), 4.52 (2H, d, J=6 Hz), 2.73-2.69 (2H, m), 2.56-2.51 (2H, m).

Example 13

4-({5-[(3,4-Difluorophenyl)methylcarbamoyl]-4-hydroxypyrimidin-2-yl}amino)-4-oxobutanoic acid

[Formula 22]

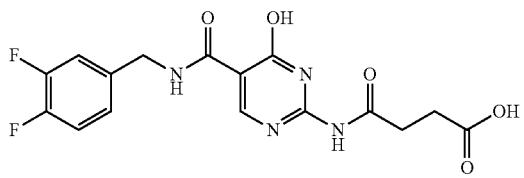

The title compound was obtained in accordance with the method of Example 6, but using (3,4-difluorophenyl)methanamine instead of (3-phenylphenyl)methanamine.

MS m/z: 381 (M+H)+;
¹H-NMR (500 MHz, DMSO-d₆) δ: 8.34 (1H, brs), 7.41-7.34 (2H, m), 7.17-7.15 (1H, m), 4.48 (2H, d, J=5 Hz), 2.73-2.69 (2H, m), 2.56-2.54 (2H, m).

Example 14

4-{[4-Hydroxy-5-(m-tolylmethylcarbamoyl)pyrimidin-2-yl]amino}-4-oxobutanoic acid

[Formula 23]

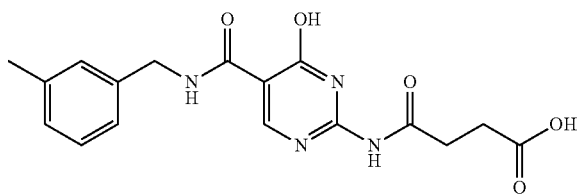

The title compound was obtained in accordance with the method of Example 6, but using m-tolylmethanamine instead of (3-phenylphenyl)methanamine.

MS m/z: 359 (M+H)+;
¹H-NMR (400 MHz, DMSO-d₆) δ: 8.35 (1H, s), 7.22 (1H, t, J=7 Hz), 7.11-7.06 (3H, m), 4.46 (2H, d, J=5 Hz), 2.72-2.67 (2H, m), 2.56-2.53 (2H, m), 2.29 (3H, s).

Example 15

4-{[4-Hydroxy-5-(1-naphthylmethylcarbamoyl)pyrimidin-2-yl]amino}-4-oxobutanoic acid

[Formula 24]

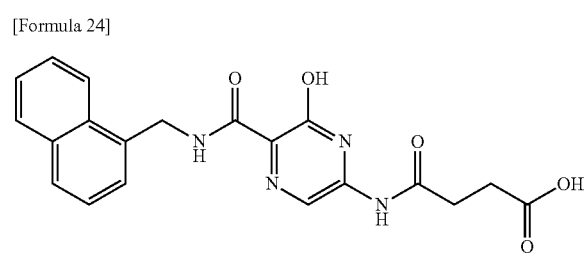 [SMILES: O=C(O)CCC(=O)Nc1cnc(C(=O)NCc2cccc3ccccc23)c(O)n1]

The title compound was obtained in accordance with the method of Example 6, but using 1-naphthylmethanamine instead of (3-phenylphenyl)methanamine.

MS m/z: 395 (M+H)+;
¹H-NMR (400 MHz, DMSO-d₆) δ: 8.39 (1H, brs), 8.12 (1H, t, J=7 Hz), 7.97 (1H, dd, J=7 Hz, 2 Hz), 7.88 (1H, d, J=7 Hz), 7.60-7.53 (2H, m), 7.51-7.46 (2H, m), 4.97 (2H, t, J=6 Hz), 2.74-2.65 (2H, m), 2.55-2.51 (2H, m).

Example 16

4-{[4-Hydroxy-5-(2-naphthylmethylcarbamoyl)pyrimidin-2-yl]amino}-4-oxobutanoic acid

[Formula 25]

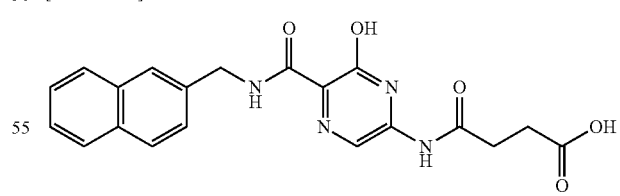

The title compound was obtained in accordance with the method of Example 6, but using 2-naphthylmethanamine instead of (3-phenylphenyl)methanamine.

MS m/z: 395 (M+H)+;
¹H-NMR (500 MHz, DMSO-d₆) δ: 8.40 (1H, brs), 7.90-7.87 (3H, m), 7.80 (1H, s), 7.52-7.47 (3H, m), 4.67 (2H, d, J=6 Hz), 2.74-2.70 (2H, m), 2.56-2.51 (2H, m).

Example 17

4-({5-[(3-Cyclopentylphenyl)methylcarbamoyl]-4-hydroxypyrimidin-2-yl}amino)-4-oxobutanoic acid

[Formula 26]

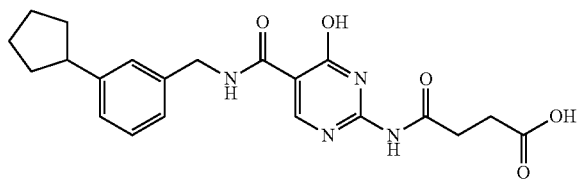

(1) Tert-butyl N-tert-butoxycarbonyl-N-{[3-(cyclopenten-1-yl)phenyl]methyl}carbamate

[Formula 27]

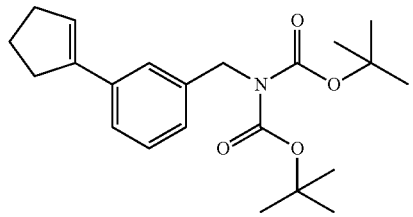

Tert-butyl N-[(3-bromophenyl)methyl]-N-tert-butoxycarbonylcarbamate (5.40 g) was dissolved in a mixed solvent of toluene (150 mL), ethanol (100 mL), and water (100 mL). To the solution, 2-(cyclopenten-1-yl)-4,4,5,5-tetramethyl-1,3,2-dioxaborolane (3.26 g), tetrakis(triphenylphosphine) palladium complex (1.62 g), and sodium carbonate (4.45 g) were added at room temperature, and the mixture was then heated to reflux for 19 hours. The reaction solution was cooled to room temperature, and ethyl acetate was then added thereto for separation into organic and aqueous layers. The organic layer was washed with water and concentrated under reduced pressure, and the obtained residue was then purified by chromatography on a silica gel column (Moritex Corporation, elution solvent: hexane/ethyl acetate) to obtain the title compound (4.92 g).

$^1$H-NMR (400 MHz, CDCl$_3$) δ: 7.35 (1H, s), 7.34 (1H, d, J=2 Hz), 7.25 (1H, dd, J=8 Hz, 2 Hz), 7.14 (1H, d, H=8 Hz), 6.19-6.13 (1H, m), 4.77 (2H, s), 2.73-2.65 (2H, m), 2.56-2.48 (2H, m), 2.05-1.96 (2H, m), 1.46 (18H, s).

(2) Tert-butyl N-tert-butoxycarbonyl-N-[(3-cyclopentylphenyl)methyl]carbamate

[Formula 28]

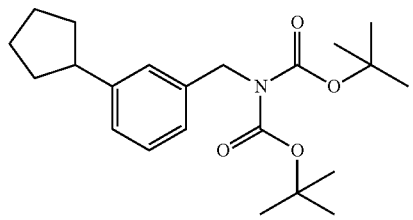

Tert-butyl N-tert-butoxycarbonyl-N-{[3-(cyclopenten-1-yl)phenyl]methyl}carbamate (4.92 g) was dissolved in ethyl acetate (150 mL). To the solution, 10% palladium-carbon (0.50 g) was added, and the mixture was then stirred at room temperature for 2 hours under a hydrogen atmosphere. The reaction solution was filtered through celite. The filtrate was concentrated under reduced pressure to obtain the title compound (4.70 g).

$^1$H-NMR (400 MHz, CDCl$_3$) δ: 7.25-7.06 (4H, m), 4.76 (2H, s), 3.02-2.89 (1H, m), 2.10-1.99 (2H, m), 1.84-1.73 (2H, m), 1.73-1.62 (2H, m), 1.61-1.50 (2H, m), 1.45 (18H, s).

(3) (3-Cyclopentylphenyl)methanamine hydrochloride

[Formula 29]

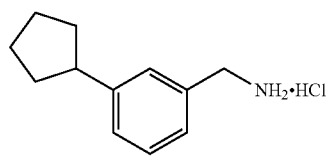

To tert-butyl N-tert-butoxycarbonyl-N-[(3-cyclopentylphenyl)methyl]carbamate (4.70 g), a solution of hydrogen chloride in ethyl acetate (4 M, 50 mL) was added, and the mixture was then stirred at room temperature for 2 hours. The reaction solution was concentrated under reduced pressure, and ether (200 mL) was added to the residue. The resulting suspension was filtered, and the product collected by filtration was dried under reduced pressure to obtain the title compound (2.64 g).

MS m/z: 176 (M+H)$^+$;
$^1$H-NMR (400 MHz, DMSO-D$_6$) δ: 8.29 (3H, brs), 7.39 (1H, s), 7.37-7.21 (3H, m), 3.99 (2H, s), 3.02-2.90 (1H, m), 2.07-1.95 (2H, m), 1.86-1.73 (2H, m), 1.72-1.60 (2H, m), 1.60-1.49 (2H, m).

(4) 4-({5-[(3-Cyclopentylphenyl)methylcarbamoyl]-4-hydroxypyrimidin-2-yl}amino)-4-oxobutanoic acid The title compound was obtained in accordance with the method of Example 6, but using (3-cyclopentylphenyl)methanamine hydrochloride instead of (3-phenylphenyl)methanamine.

MS m/z: 413 (M+H)$^+$;
$^1$H-NMR (500 MHz, DMSO-d$_6$) δ: 8.35 (1H, brs), 7.24 (1H, t, J=8 Hz), 7.19 (1H, s), 7.14 (1H, d, J=7 Hz), 7.10 (1H, d, J=7 Hz), 4.47 (2H, d, J=5 Hz), 2.97-2.91 (1H, m), 2.72-2.68 (2H, m), 2.56-2.53 (2H, m), 2.02-1.97 (2H, m), 1.79-1.72 (2H, m), 1.67-1.59 (2H, m), 1.54-1.47 (2H, m).

Example 18

4-({4-Hydroxy-5-[(3-phenylphenyl)methylcarbamoyl]-2-pyridyl}amino)-4-oxobutanoic acid

[Formula 30]

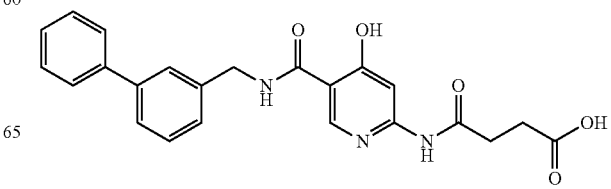

(1) Methyl 6-[(2,4-dimethoxyphenyl)methylamino]-4-methoxypyridine-3-carboxylate

[Formula 31]

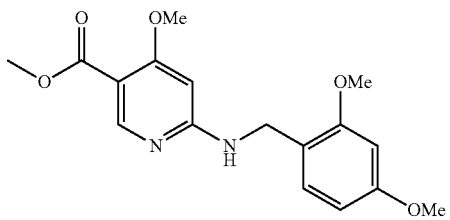

To a solution of methyl 6-chloro-4-methoxypyridine-3-carboxylate (1.09 g) in N,N-dimethylacetamide (12 mL), 2,4-dimethoxybenzylamine (1.35 g) and potassium carbonate (2.24 g) were added at room temperature, and the mixture was stirred at 120° C. for 19 hours. The reaction solution was cooled to room temperature, then diluted with ethyl acetate, and washed with water and saturated saline. The organic layer was dried over anhydrous sodium sulfate and then filtered, and the filtrate was concentrated under reduced pressure. The obtained residue was purified by chromatography on a silica gel column (Biotage Ltd., elution solvent: hexane/ethyl acetate) to obtain the title compound (1.16 g).

$^1$H-NMR (400 MHz, CDCl$_3$) δ: 8.58 (1H, s), 7.19 (1H, d, J=8 Hz), 6.47 (1H, d, J=2 Hz), 6.44 (1H, dd, J=8 Hz, 2 Hz), 5.83 (1H, s), 5.35 (1H, t, J=6 Hz), 4.43 (2H, d, J=6 Hz), 3.86 (3H, s), 3.84 (3H, s), 3.82 (3H, s), 3.80 (3H, s).

(2) 6-[(2,4-Dimethoxyphenyl)methylamino]-4-methoxypyridine-3-carboxylic acid

[Formula 32]

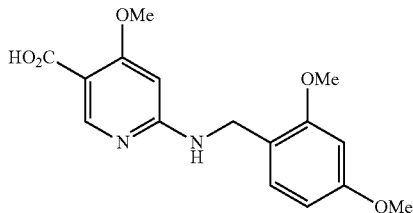

Methyl 6-[(2,4-dimethoxyphenyl)methylamino]-4-methoxypyridine-3-carboxylate (1.16 g) was dissolved in a mixed solvent of tetrahydrofuran (10 mL) and methanol (10 mL). An aqueous potassium hydroxide solution (1 M, 7 mL) was added to the solution at room temperature. The reaction solution was stirred for 15 hours, and the organic solvent was then distilled off under reduced pressure. The obtained residue was diluted with water, and hydrochloric acid (1 M, 7.5 mL) was then added thereto. The resulting suspension was filtered, and the product collected by filtration was washed with water and dried under reduced pressure to obtain the title compound (0.890 g).

$^1$H-NMR (400 MHz, CDCl$_3$) δ: 8.68 (1H, s), 7.20 (1H, d, J=8 Hz), 6.47 (1H, d, J=2 Hz), 6.44 (1H, dd, J=8 Hz, 2 Hz), 5.86 (1H, s), 4.45 (2H, d, J=6 Hz), 3.93 (3H, s), 3.84 (3H, s), 3.80 (3H, s).

(3) Tert-butyl 4-[(2,4-dimethoxyphenyl)methyl-{4-methoxy-5-[(3-phenylphenyl)methylcarbamoyl]-2-pyridyl}amino]-4-oxobutanoate

[Formula 33]

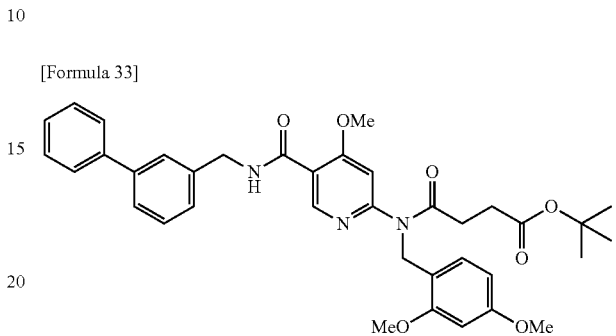

To a solution of 6-[(2,4-dimethoxyphenyl)methylamino]-4-methoxypyridine-3-carboxylic acid (382 mg), 3-phenylbenzylamine (220 mg), and triethylamine (0.67 mL) in N,N-dimethylformamide (4 mL), 2-(1H-7-azabenzotriazol-1-yl)-1,1,3,3-tetramethyluronium hexafluorophosphate (502 mg) was added at room temperature, and the mixture was stirred for 18 hours. A saturated aqueous ammonium chloride solution and water were added to the reaction solution, followed by extraction with ethyl acetate. The organic layer was washed with saturated saline, dried over anhydrous sodium sulfate, and then filtered, and the filtrate was concentrated under reduced pressure. The obtained residue and 4-tert-butoxy-4-oxobutanoic acid (418 mg) were dissolved in N,N-dimethylformamide (4 mL). To the solution, N,N-diisopropylethylamine (0.84 mL) and 2-(1H-7-azabenzotriazol-1-yl)-1,1,3,3-tetramethyluronium hexafluorophosphate (913 mg) were added at room temperature, and the mixture was stirred at 100° C. for 2 hours. 4-Tert-butoxy-4-oxobutanoic acid (418 mg), N,N-diisopropylethylamine (0.84 mL), and 2-(1H-7-azabenzotriazol-1-yl)-1,1,3,3-tetramethyluronium hexafluorophosphate (913 mg) were further added thereto, and the mixture was stirred at 100° C. for 20 hours. N,N-Dimethylformamide (4 mL), 4-tert-butoxy-4-oxobutanoic acid (836 mg), N,N-diisopropylethylamine (0.84 mL), and 2-(1H-7-azabenzotriazol-1-yl)-1,1,3,3-tetramethyluronium hexafluorophosphate (1830 mg) were further added thereto, and the mixture was stirred at 100° C. for 24 hours. The reaction solution was cooled to room temperature, diluted with ethyl acetate, and then washed with a saturated aqueous ammonium chloride solution, water, and saturated saline. The organic layer was dried over anhydrous sodium sulfate and then filtered, and the filtrate was concentrated under reduced pressure. The obtained residue was purified by chromatography on a silica gel column (Biotage Ltd., elution solvent: hexane/ethyl acetate) to obtain a mixture (345 mg) containing the title compound.

MS m/z: 640 (M+H)$^+$.

(4) 4-({4-Hydroxy-5-[(3-phenylphenyl)methylcarbamoyl]-2-pyridyl}amino)-4-oxobutanoic acid A solution of the mixture (345 mg) containing tert-butyl 4-[(2,4-dimethoxyphenyl)methyl-{4-methoxy-5-[(3-phenylphenyl)methylcarbamoyl]-2-pyridyl}amino]-4-oxobutanoate in trifluoroacetic acid (4 mL) was left standing at room temperature for 17 hours. Ether (60 mL) was added to the reaction solution. The resulting suspension was filtered, and the product collected by filtration was washed with ether and dried under reduced pressure. To the obtained residue, a solution of boron tribromide in dichloromethane (1 M, 6 mL) was added at room temperature, and the mixture was stirred at 40° C. for 6 hours. The reaction mixture was cooled to room temperature, and water was then added thereto. The resulting suspension was filtered, and the product collected by filtration was washed with water and ether. The obtained residue was suspended in ethanol, and the suspension was shaken for 15 minutes in an ultrasonic bath and then filtered. The product collected by filtration was dried under reduced pressure to obtain the title compound (56.7 mg).

MS m/z: 420 (M+H)$^+$;

$^1$H-NMR (400 MHz, DMSO-D$_6$) δ: 8.34 (1H, d, J=6 Hz), 7.64-7.54 (4H, m), 7.49-7.29 (5H, m), 5.95 (1H, s), 4.57 (2H, d, J=6 Hz), 2.66-2.62 (2H, m), 2.56-2.52 (2H, m).

Example 19

4-Oxo-4-({5-[(4-phenylphenyl)methoxymethyl]-2-pyridyl}amino)butanoic acid

[Formula 34]

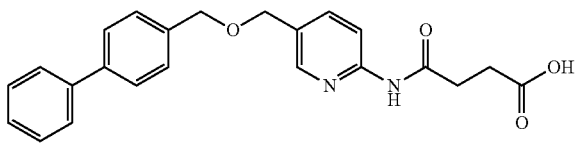

(1)
2-Chloro-5-[(4-phenylphenyl)methoxymethyl]pyridine

[Formula 35]

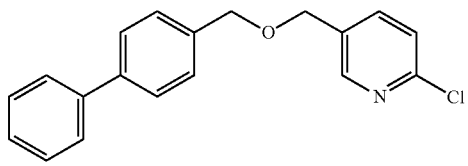

To a solution of (6-chloro-3-pyridyl)methanol (0.538 g) in tetrahydrofuran (15 mL), sodium hydride (63% oil, 0.182 g) was added at 0° C., and the mixture was stirred at room temperature for 30 minutes. 1-(Bromomethyl)-4-phenylbenzene (0.932 g) was added to the reaction solution at room temperature, and the mixture was stirred at 50° C. for 3 hours. The reaction solution was cooled to 0° C., and a saturated aqueous ammonium chloride solution was added thereto, followed by extraction with dichloromethane. The organic layer was washed with saturated saline, dried over anhydrous sodium sulfate, and then filtered, and the filtrate was concentrated under reduced pressure. The obtained residue was purified by chromatography on a silica gel column (Yamazen Corporation, elution solvent: hexane/ethyl acetate) to obtain the title compound (0.896 g).

1H-NMR (400 MHz, CDCl$_3$) δ: 8.38 (1H, s), 7.69 (1H, d, J=4 Hz), 7.65-7.54 (4H, m), 7.52-7.30 (5H, m), 7.29-7.22 (1H, m), 4.62 (2H, s), 4.57 (2H, s).

(2)
5-[(4-Phenylphenyl)methoxymethyl]pyridin-2-amine

[Formula 36]

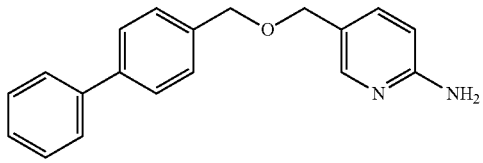

To a solution of 2-chloro-5-[(4-phenylphenyl)methoxymethyl]pyridine (0.206 g) in tetrahydrofuran (10 mL), tris(dibenzylideneacetone)dipalladium (63 mg), 2-(dicyclohexylphosphino)biphenyl (48 mg), and a solution of lithium bis(trimethylsilyl)amide in tetrahydrofuran (1.0 M, 1.0 mL) were added at room temperature, and the mixture was heated to reflux for 22 hours under a nitrogen atmosphere. Hydrochloric acid (2 M, 10 mL) was added to the reaction solution, and the mixture was further stirred for 30 minutes. The reaction solution was cooled to room temperature, and sodium carbonate was gradually added thereto, and subsequently, water was added thereto, followed by extraction with dichloromethane. The organic layer was washed with saturated saline, dried over anhydrous sodium sulfate, and then filtered, and the filtrate was concentrated under reduced pressure. The obtained residue was purified by chromatography on a silica gel column (Yamazen Corporation, elution solvent: dichloromethane/methanol) to obtain the title compound (0.189 g).

1H-NMR (400 MHz, CDCl$_3$) δ: 8.06 (1H, d, J=4 Hz), 7.63-7.57 (4H, m), 7.50 (1H, dd, J=8 Hz, 4 Hz), 7.47-7.40 (4H, m), 7.35 (1H, t, J=8 Hz), 6.52 (1H, d, J=8 Hz), 4.56 (2H, s), 4.44 (2H, s), 4.40 (2H, brs).

(3) Methyl 4-oxo-4-({5-[(4-phenylphenyl)methoxymethyl]-2-pyridyl}amino)butanoate

[Formula 37]

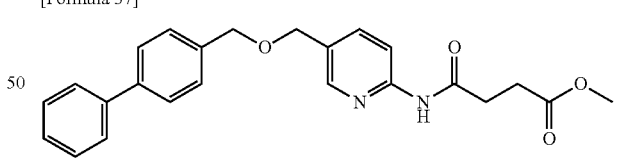

To a solution of 5-[(4-phenylphenyl)methoxymethyl]pyridin-2-amine (0.189 g) in N,N-dimethylformamide (6.0 mL), N,N-diisopropylethylamine (0.453 mL), 4-methoxy-4-oxobutanoic acid (0.174 g), and 2-(1H-7-azabenzotriazol-1-yl)-1,1,3,3-tetramethyluronium hexafluorophosphate (0.376 g) were added at room temperature, and the mixture was stirred at 80° C. for 2 hours. The reaction solution was cooled to room temperature, and water was then added thereto, followed by extraction with ethyl acetate. The organic layer was washed with saturated saline, dried over anhydrous sodium sulfate, and then filtered, and the filtrate was concentrated under reduced pressure. The obtained residue was purified by chromatography on a silica gel column (Yamazen Corporation, elution solvent: dichloromethane/ethyl acetate) to obtain the title compound (0.171 g).

1H-NMR (400 MHz, CDCl$_3$) δ: 8.27 (1H, d, J=4 Hz), 8.18 (1H, d, J=8 Hz), 8.09 (1H, brs), 7.72 (1H, dd, J=8 Hz, 4 Hz), 7.64-7.57 (4H, m), 7.48-7.41 (4H, m), 7.36 (1H, t, J=8 Hz), 4.60 (2H, s), 4.54 (2H, s), 3.72 (3H, s), 2.80-2.69 (4H, m).

(4) 4-Oxo-4-({5-[(4-phenylphenyl)methoxymethyl]-2-pyridyl}amino)butanoic acid

Methyl 4-oxo-4-({5-[(4-phenylphenyl)methoxymethyl]-2-pyridyl}amino)butanoate (0.168 g) was dissolved in a mixed solvent of tetrahydrofuran (3 mL) and methanol (1 mL). To the solution, an aqueous sodium hydroxide solution (1 M, 0.830 mL) was added at room temperature, and the mixture was stirred for 1 hour. Hydrochloric acid (1 M, 0.830 mL) was added to the reaction solution, and the mixture was stirred at 0° C. The resulting suspension was filtered, and the product collected by filtration was washed with water and dried under reduced pressure to obtain the title compound (0.150 g).

MS m/z: 389 (M−H)$^+$;

1H-NMR (400 MHz, DMSO-d$_6$) δ: 12.13 (1H, s), 10.56 (1H, s), 8.30 (1H, d, J=4 Hz), 8.07 (1H, d, J=8 Hz), 7.77 (1H, dd, J=8 Hz, 4 Hz), 7.70-7.65 (4H, m), 7.51-7.43 (4H, m), 7.36 (1H, t, J=8 Hz), 4.57 (2H, s), 4.53 (2H, s), 2.66-2.60 (2H, m), 2.53-2.47 (2H, m).

Example 20

4-[(5-{[4-(2-Cyanophenyl)phenyl]methoxymethyl}-2-pyridyl)amino]-4-oxobutanoic acid

[Formula 38]

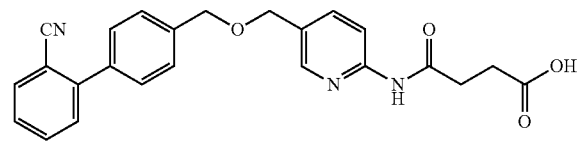

The title compound was obtained in accordance with the method of Example 19, but using 2-[4-(bromomethyl)phenyl]benzonitrile instead of 1-(bromomethyl)-4-phenylbenzene.

MS m/z: 414 (M−H)$^+$;

1H-NMR (400 MHz, DMSO-d$_6$) δ: 12.14 (1H, s), 10.57 (1H, s), 8.32 (1H, d, J=4 Hz), 8.08 (1H, d, J=8 Hz), 7.96 (1H, dd, J=8 Hz, 4 Hz), 7.85-7.78 (2H, m), 7.63-7.50 (6H, m), 4.62 (2H, s), 4.56 (2H, s), 2.69-2.60 (2H, m), 2.54-2.48 (2H, m).

FORMULATION EXAMPLES

Formulation Example 1

Injection 1.5% by weight of a compound of the Examples is stirred in 10% by volume of propylene glycol, then adjusted to a fixed volume with water for injection, and subsequently sterilized to obtain an injection.

Formulation Example 2

Hard Capsule 100 mg of a powdery compound of the Examples, 128.7 mg of lactose, 70 mg of cellulose, and 1.3 mg of magnesium stearate are mixed, and passed through 60 mesh sieve, and subsequently the resulting powders are put into 250 mg of No. 3 gelatin capsule to obtain capsules.

Formulation Example 3

Tablet 100 mg of a powdery compound of the Examples, 124 mg of lactose, 25 mg of cellulose, and 1 mg of magnesium stearate are mixed, and tableted with a tablet-making machine to obtain tablets each having 250 mg. This tablet can be sugar-coated as necessary.

Test Example

The pharmacological activity of the compounds of the present invention was confirmed by the testing indicated below.

In vitro erythropoietin (EPO) induction activity of test compounds was evaluated using human liver cancer-derived cell line Hep3B (ATCC, Manassas, Va.). Hep3B cells were cultured overnight at 37° C. in Dulbecco's modified Eagle's medium (DMEM) in the presence of 10% fetal bovine serum (FBS) (24-well plate, $1.0 \times 10^5$ cells/well). After replacing with fresh DMEM (+10% FBS) containing a test compound dissolved in 0.5% dimethyl sulfoxide (DMSO) (prepared to a concentration of 12.5 µM) or a solvent control (0.5% DMSO), the cells were cultured for 32 hours at 37° C. After recovering the culture supernatant, EPO concentration in the culture supernatant was quantified using human EPO ELISA kits (StemCell Technologies).

The EPO concentration using a compound of each example as a test compound was expressed as a multiple of the EPO concentration in the control. The results are shown in Table 1. The compounds of the present invention or pharmacologically acceptable salts thereof demonstrated a superior EPO production-enhancing activity, and are useful as medicaments (in particular, medicaments for prophylaxis or treatment of anemia).

TABLE 1

| Number of Compound of Example | EPO concentration (multiple) |
|---|---|
| Control (0.5% DMSO) | 1 |
| 1 | 3.6 |
| 2 | 7.9 |
| 3 | 9.5 |
| 5 | 6.3 |
| 6 | 3.7 |
| 9 | 16 |
| 10 | 10 |
| 11 | 7.5 |
| 12 | 7.2 |
| 13 | 13 |
| 14 | 3.0 |
| 17 | 4.4 |

Industrial Applicability

The compounds of the present invention or pharmacologically acceptable salts thereof have a superior EPO production-enhancing activity, and are useful for diseases caused by decreased EPO or the like. Specifically, the compounds of the present invention or pharmacologically acceptable salts thereof are useful as medicaments for the prophylaxis and/or treatment of anemia, preferably nephrogenic anemia, anemia of prematurity, anemia incidental to chronic diseases, anemia incidental to cancer chemotherapy, cancerous anemia, inflammation-associated anemia, or anemia incidental to congestive heart failure, more preferably anemia incidental to chronic kidney disease, and can also be used as medicaments for the prophylaxis and/or treatment of ischemic cerebrovascular disease or the like.

The invention claimed is:
1. A compound represented by the following general formula (1):

[Formula 1]

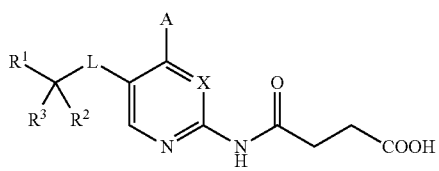

or a pharmacologically acceptable salt thereof,
wherein
$R^1$ represents an aromatic hydrocarbon ring group which may have 1 or 2 substituents independently selected from substituent group α, or an aromatic heterocyclic group which may have 1 or 2 substituents independently selected from substituent group α;
substituent group α represents the group consisting of a halogen atom, a $C_1$-$C_4$ alkyl group, a halo $C_1$-$C_4$ alkyl group, a $C_1$-$C_4$ alkoxy group, a $C_3$-$C_6$ cycloalkyl group, and an aromatic hydrocarbon ring group which may be substituted with $R^4$;
$R^2$ represents a hydrogen atom, a $C_1$-$C_4$ alkyl group, or a 4- to 7-membered heterocycloalkyl group;
$R^3$ represents a hydrogen atom or a $C_1$-$C_4$ alkyl group;
$R^4$ represents a cyano group, a halogen atom, or a $C_1$-$C_4$ alkoxy group;
A represents a hydrogen atom or a hydroxy group;
L represents a group represented by the formula —NHCO— or a group represented by the formula —OCH$_2$—; and
X represents a nitrogen atom or a group represented by the formula =CH—.

2. A compound or a pharmacologically acceptable salt thereof according to claim 1, wherein $R^1$ is a phenyl group, a naphthyl group, a pyridyl group, a pyrimidinyl group, a pyrazinyl group, or a pyridazinyl group which may have 1 or 2 substituents independently selected from substituent group α.

3. A compound or a pharmacologically acceptable salt thereof according to claim 1, wherein $R^1$ is a phenyl group, a naphthyl group, or a pyridyl group which may have 1 or 2 substituents independently selected from substituent group α.

4. A compound or a pharmacologically acceptable salt thereof according to claim 1, wherein $R^1$ is a phenyl group or a pyridyl group which may have 1 or 2 substituents independently selected from substituent group α.

5. A compound or a pharmacologically acceptable salt thereof according to claim 1, wherein
the substituent group α is the group consisting of a fluorine atom, a chlorine atom, a methyl group, a trifluoromethyl group, a methoxy group, a cyclopentyl group, and a phenyl group which may be substituted with $R^4$, and
$R^4$ is a cyano group or a methoxy group.

6. A compound or a pharmacologically acceptable salt thereof according to claim 1, wherein the substituent group α is the group consisting of a fluorine atom, a chlorine atom, a trifluoromethyl group, a methoxy group, and a phenyl group which may be substituted with $R^4$, and
$R^4$ is a methoxy group.

7. A compound or a pharmacologically acceptable salt thereof according to claim 1, wherein $R^2$ is a hydrogen atom, a methyl group, or a tetrahydropyranyl group.

8. A compound or a pharmacologically acceptable salt thereof according to claim 1, wherein $R^3$ is a hydrogen atom or a methyl group.

9. A compound or a pharmacologically acceptable salt thereof according to claim 1, wherein A is a hydroxy group.

10. A compound or a pharmacologically acceptable salt thereof according to claim 1, wherein L is a group represented by the formula —NHCO—.

11. A compound or a pharmacologically acceptable salt thereof according to claim 1, wherein X is a nitrogen atom.

12. A compound or a pharmacologically acceptable salt thereof according to claim 1, selected from the following:
4-({5-[(2,4-dichlorophenyl)methylcarbamoyl]-4-hydroxypyrimidin-2-yl}amino)-4-oxobutanoic acid,
4-({5-[(2,4-difluorophenyl)methylcarbamoyl]-4-hydroxypyrimidin-2-yl}amino)-4-oxobutanoic acid,
4-({5-[(2-chloro-4-fluorophenyl)methylcarbamoyl]-4-hydroxypyrimidin-2-yl}amino)-4-oxobutanoic acid,
4-{[4-hydroxy-5-(p-tolylmethylcarbamoyl)pyrimidin-2-yl]amino}-4-oxobutanoic acid,
4-({5-[(4-fluoro-3-phenylphenyl)methylcarbamoyl]-4-hydroxypyrimidin-2-yl}amino)-4-oxobutanoic acid,
4-({4-hydroxy-5-[(3-phenylphenyl)methylcarbamoyl]pyrimidin-2-yl}amino)-4-oxobutanoic acid,
4-[(5-{[4-(2-cyanophenyl)phenyl]methylcarbamoyl}-4-hydroxypyrimidin-2-yl)amino]-4-oxobutanoic acid,
4-[(5-{[3-(2-cyanophenyl)phenyl]methylcarbamoyl}-4-hydroxypyrimidin-2-yl)amino]-4-oxobutanoic acid,
4-[(4-hydroxy-5-{[(6-methoxypyridin-3-yl)(tetrahydro-2H-pyran-4-yl)methyl]carbamoyl}pyrimidin-2-yl)amino]-4-oxobutanoic acid,
4-{[4-hydroxy-5-({1-[6-(4-methoxyphenyl)pyridin-3-yl]-1-methylethyl}carbamoyl)pyrimidin-2-yl]amino}-4-oxobutanoic acid,
4-[(4-hydroxy-5-{[3-(trifluoromethyl)phenyl]methylcarbamoyl}pyrimidin-2-yl)amino]-4-oxobutanoic acid,
4-({5-[(3-fluorophenyl)methylcarbamoyl]-4-hydroxypyrimidin-2-yl}amino)-4-oxobutanoic acid,
4-({5-[(3,4-difluorophenyl)methylcarbamoyl]-4-hydroxypyrimidin-2-yl}amino)-4-oxobutanoic acid,
4-{[4-hydroxy-5-(m-tolylmethylcarbamoyl)pyrimidin-2-yl]amino}-4-oxobutanoic acid,
4-{[4-hydroxy-5-(1-naphthylmethylcarbamoyl)pyrimidin-2-yl]amino}-4-oxobutanoic acid,
4-{[4-hydroxy-5-(2-naphthylmethylcarbamoyl)pyrimidin-2-yl]amino}-4-oxobutanoic acid,
4-({5-[(3-cyclopentylphenyl)methylcarbamoyl]-4-hydroxypyrimidin-2-yl}amino)-4-oxobutanoic acid,
4-({4-hydroxy-5-[(3-phenylphenyl)methylcarbamoyl]-2-pyridyl}amino)-4-oxobutanoic acid,
4-oxo-4-({5-[(4-phenylphenyl)methoxymethyl]-2-pyridyl}amino)butanoic acid, and
4-[(5-{[4-(2-cyanophenyl)phenyl]methoxymethyl}-2-pyridyl)amino]-4-oxobutanoic acid.

13. A pharmaceutical composition containing as an active ingredient a compound or a pharmacologically acceptable salt thereof according to claim 1.

14. A method for producing erythropoietin in a human comprising, administering a pharmacologically effective amount of a compound or a pharmacologically acceptable salt thereof according to claim 1 to a human.

15. A method for the treatment of a disease in a human caused by decreased erythropoietin, comprising administering a pharmacologically effective amount of a compound or a pharmacologically acceptable salt thereof according to claim 1 to the human.

16. A method according to claim 15, wherein the disease is anemia.

* * * * *